(12) United States Patent
Song et al.

(10) Patent No.: US 10,799,529 B2
(45) Date of Patent: Oct. 13, 2020

(54) COMPOSITION FOR PREVENTING OR TREATING SPINAL CORD INJURY COMPRISING IMIDAZOLE-POLY(ORGANO-PHOSPHAZENE) HYDROGEL

(71) Applicant: KOREA INSTITUTE OF SCIENCE AND TECHNOLOGY, Seoul (KR)

(72) Inventors: Soo Chang Song, Seoul (KR); Young-min Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/567,027

(22) Filed: Sep. 11, 2019

(65) Prior Publication Data

US 2020/0085860 A1 Mar. 19, 2020

(30) Foreign Application Priority Data

Sep. 14, 2018 (KR) .................. 10-2018-0110436

(51) Int. Cl.
*A61K 31/80* (2006.01)
*A61P 25/00* (2006.01)

(52) U.S. Cl.
CPC .............. *A61K 31/80* (2013.01); *A61P 25/00* (2018.01)

(58) Field of Classification Search
CPC ................................. A61K 31/80; A61P 25/00
See application file for complete search history.

(56) References Cited

FOREIGN PATENT DOCUMENTS

KR 20050012533 A 2/2005

OTHER PUBLICATIONS

Bae Hoon Lee, et al., Synthesis and Characterization of Biodegradable ThermosensitivePoly(organophosphazene) Gels, Macromolecules 2004, 37:4533-4537.
Meng Deng et al., Polyphosphazene polymers for tissue engineering: an analysis of material synthesis, characterization and applications Soft Matter, 2010, vol. 6, p. 3119-3132.
Notice of Allowance issued by the Korean Intellectual Patent Office dated Dec. 18, 2019 for the priority application KR 10-2018-0110436 of the above cited US application, citing the references submitted herewith.
A. Hejcl et al. "Biocompatible Hydrogels in Spinal Cord Injury Repair," Physiological Research, 2008, S121-S132, vol. 57.

*Primary Examiner* — Sikarl A Witherspoon
(74) *Attorney, Agent, or Firm* — Cantor Colburn LLP

(57) ABSTRACT

The present disclosure relates to a pharmaceutical composition for preventing or treating spinal cord injury comprising an imidazole-poly(organophosphazene) hydrogel or a pharmaceutically acceptable salt thereof, a method for preventing or treating spinal cord injury, and a food composition for preventing or ameliorating spinal cord injury.
The imidazole-poly(organophosphazene) hydrogel of the present disclosure has the effect of regenerating the extracellular matrix (ECM) by filling cystic cavities and can thus be effectively used for the prevention and treatment of spinal cord injury by a simple injection method.

8 Claims, 44 Drawing Sheets

Specification includes a Sequence Listing.

COMPOSITION FOR PREVENTING OR TREATING SPINAL CORD INJURY COMPRISING IMIDAZOLE-POLY(ORGANOPHOSPHAZENE) HYDROGEL

SEQUENCE LISTING

This disclosure incorporates by reference a sequence listing submitted as an ASCII text file named 8FS4001.TXT of size 4.0 KB, created Dec. 3, 2019.

TECHNICAL FIELD

The present disclosure relates to a pharmaceutical composition for preventing or treating spinal cord injury containing an imidazole-poly(organophosphazene) hydrogel or a pharmaceutically acceptable salt thereof, a method for preventing or treating spinal cord injury comprising administering the imidazole-poly(organophosphazene) hydrogel or the pharmaceutically acceptable salt thereof, and a food composition for preventing or ameliorating spinal cord injury.

BACKGROUND ART

Injury or vascular damage to the central nervous system (CNS) is somewhat complicated by the development of fluid-filled cystic cavities.

Such fluid-filled cystic cavities can have a particularly devastating influence after spinal cord injury (SCI) because the spinal cord has a cylindrical structure with a small cross-sectional area into which many important axonal tracts are crowded. Cystic lesions filled with cerebrospinal fluid are frequently present at the epicenter of a disease during its chronic stages. Furthermore, more than 50% of patients develop post-traumatic spinal cord cysts or syringomyelia.

A lack of extracellular matrix (ECM) and/or vascularization hinders infiltration of cellular elements and regeneration of axons in the cavity space. Additionally, survival and integration of transplanted cells for therapeutic purposes is substantially compromised in the presence of a cystic cavity. Therefore, the development of a cystic cavity poses a formidable hurdle for successful tissue repair after CNS injuries. Thus, studies should target cystic cavities for the treatment of spinal cord injury.

Biomaterial-based treatment has been proposed as a strategy to promote tissue repair by bridging cavity spaces (Hejcl, A. et al. Biocompatible hydrogels in spinal cord injury repair. *Physiol. Res.* 57, S121-S132 (2008)). Implanting various tissue-engineered scaffolds or matrices has been reported to reduce cyst formation. However, in most cases of human spinal cord injury, the surgical operations (e.g., implanting of scaffolds and matrices, etc.) still have a problem in that these operations can aggravate functional deficits.

SUMMARY

Technical Problem

The present inventors have made efforts to discover a material which can be applied to subjects by a simple method of direct injection and thereby remove cystic cavities and lead to recovery from spinal cord injury. As a result, they have confirmed that simple injection of imidazole-poly (organophosphazenes) (I-5), which is a hydrogel with sol-gel transition behavior, can remove cystic cavities, thereby completing the present disclosure.

Technical Solution

An object of the present disclosure is to provide a method for the treatment of spinal cord injury, which includes administering a compound of Formula 1 below or a pharmaceutically acceptable salt thereof to a subject in need thereof.

[Formula 1]

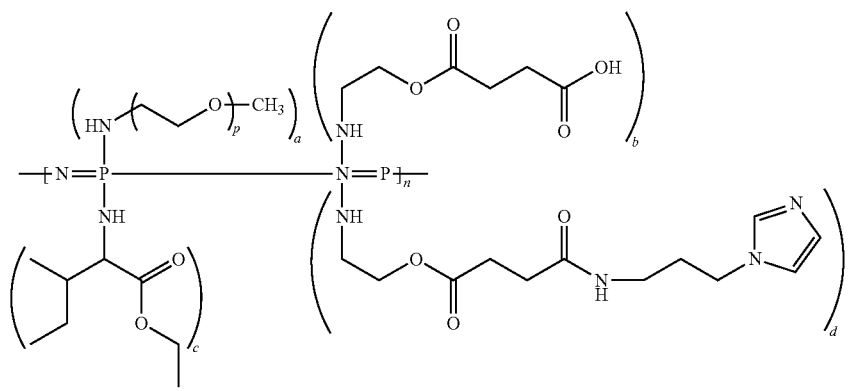

In Formula 1 above, p is in a range of 16 to 50, a, b, c, and d are values representing the amount of each substituent, which are each in a range of 0.01 to 1.9, the sum of (a+b+c+d) is 2, and n is a polymerization degree of polyphosphazene, which is in a range of 5 to 100,000.

Another object of the present disclosure is to provide a pharmaceutical composition for preventing or treating spinal cord injury, containing the compound of Formula 1 or a pharmaceutically acceptable salt thereof.

Still another object of the present disclosure is to provide a method for removing cystic cavities in the spinal cord, which contains the compound of Formula 1 or a pharmaceutically acceptable salt thereof.

Still another object of the present disclosure is to provide a food composition for preventing or ameliorating spinal cord injury, which contains the compound of Formula 1 or a sitologically acceptable salt thereof.

Advantageous Effects of the Invention

The imidazole-poly(organophosphazene) hydrogel of the present disclosure has the effect of regenerating extracellular matrix (ECM) by filling cystic cavities and can thus be effectively used for the prevention and treatment of spinal cord injury by a method of simple injection.

BRIEF DESCRIPTION OF DRAWINGS

FIGS. 2A and 2B show spectrum results, in which FIG. 2A shows the $^1$H-NMR spectrum of I-5; and FIG. 2B shows the Fourier-transform infrared spectroscopy (FT-IR) spectra of CP-2 and I-5.

FIGS. 3A to 3D show sol-gel transition properties and the results of an in vitro stability test for I-5 hydrogel, in which FIG. 3A shows temperature-dependent sol-gel transition and changes in viscosity measured by a viscometer, FIG. 3B shows visualization of a rapid gelation process, FIG. 3C shows changes in viscosity over time at 37° C., and FIG. 3D shows an in vitro stability test.

FIGS. 4A to 4C show the results of a biocompatibility test for I-5 hydrogel, in which FIG. 4A shows a graph illustrating the evaluation of cytotoxicity; FIG. 4B shows a graph illustrating the measurement results of body weight; and FIG. 4C shows images illustrating the results of visual examination of the injection areas.

FIGS. 5A to 5B show cystic cavities formed in the spinal cord 7 days after injury where lesions occurred, in which FIG. 5A shows images with regard to the formation of cystic cavities 7 days after injury; FIG. 5B shows images illustrating the cellular properties of non-cystic lesions at the epicenter 7 days after injury; and portions indicated as b' show images in which the boxed regions in FIG. 5B were magnified.

FIGS. 6A to 6E show the results of cystic cavity treatment after the injection of I-5 hydrogel, in which FIG. 6A shows the images illustrating the transverse spinal cord sections stained with eriochrome cyanine and GFAP antibodies; FIG. 6B shows the three-dimensional reconstruction of the spinal cord tissues of rats; FIG. 6C shows quantification graphs; FIG. 6D shows the images illustrating the transverse spinal cord sections at the epicenter stained with an Iba1 antibody; and FIG. 6E shows quantification of the Iba1 immunofluorescence intensity at 4 weeks after injection (5 weeks after injury).

FIGS. 8A to 8B show the images of cellular compositions of fibrotic ECM induced by I-5 hydrogel, in which FIG. 8A shows the images illustrating the presence of cell supply sources for fibrotic ECM in the rats injected with I-5 hydrogel; and FIG. 8B shows the images illustrating the presence of macrophages in fibrotic ECM.

FIG. 9A (bottom) shows the images of adjacent sections stained with fibronectin antibodies; FIG. 9A shows the images of three-dimensional reconstruction; and FIG. 9B shows a graph illustrating the quantification of cystic cavities.

FIGS. 10A to 10E show the results of fibrotic ECM remodeling mediated by MMP-9, in which FIG. 10A shows an image illustrating gelatinase activity of MMP-9 and MMP-2 in the group injected with PBS and the group injected with I-5 hydrogel; FIG. 10B shows graphs illustrating quantification of MMP-2 and MMP-9, respectively, FIG. 10C shows the images of transverse spinal cord sections in the group injected with PBS and the group injected with I-5 hydrogel; FIG. 10C (bottom) shows an image illustrating MMP-9 immunoreactive granules bounded by CD11b positive membrane-like circular structures; FIG. 10D shows the images illustrating transverse spinal cord sections stained with eriochrome cyanine and eosin from groups administered with I-5 hydrogel mixed with control group siRNA and MMP-9 siRNA, respectively; FIG. 10D shows the images of adjacent sections stained with fibronectin antibodies; FIG. 10D shows the images of three-dimensional reconstruction of the spinal cord tissue; and FIG. 10E shows a quantification graph illustrating the volumes of cystic cavities.

FIGS. 11A to 11C show the results of MMP-9 knockdown by siRNA nanoparticles, in which FIG. 11A shows a graph illustrating the measurement results of mRNA by real-time PCR; FIG. 11B shows the images confirming the MMP-9 knockdown at a protein level; FIG. 11C shows the images confirming the MMP-9 knockdown in vivo; and FIG. 11C (last panel) shows images in which the boxed regions in FIG. 11C was magnified.

FIGS. 12A to 12D show the results of interaction between macrophages and I-5 hydrogel, in which FIG. 12A shows images of Nile Red fluorescence in a macrophage cell line; FIG. 12B shows a graph illustrating the quantification of Nile Red fluorescence intensity; FIG. 12C shows an image of transverse spinal cord sections from rats injected with CP-2 hydrogel lacking an imidazole group; FIG. 12C (last panel) shows an image of three-dimensional reconstruction of the spinal cord tissue injected with CP-2 hydrogel; and FIG. 12D shows a graph illustrating the quantification of the volumes of cystic cavities.

FIGS. 13A to 13B show the sol-gel transition properties of CP-2 hydrogel and the results of an in vitro stability test, in which FIG. 13A shows a graph illustrating the temperature-dependent changes in viscosity of CP-2; and FIG. 13B shows images illustrating the results of an in vitro stability test.

FIGS. 14A to 14C show the results of locomotor recovery by the injection of I-5 hydrogel, in which FIG. 14A shows a graph illustrating the results of comparison in locomotor recovery between the group injected with PBS and the group injected with I-5 hydrogel; FIG. 14B shows images analyzed by the Catwalk software; and FIG. 14C shows graphs illustrating the quantification of the quality of locomotion used by five parameters 7 weeks after injury.

FIGS. 15A to 15F show motor neurons and myelinated white matter preserved by the injection of I-5 hydrogel, in which FIG. 15A shows images of the ventromedial region in transverse spinal cord sections; FIG. 15B shows images of MBP immunostaining in transverse spinal cord sections of the lesion epicenter from sham-operated animals; FIG. 15C shows a graph illustrating quantitative comparison of the number of motor neurons; and FIGS. 15D to 15F show graphs illustrating the quantification of fluorescence intensity of MBP immunoreactivity.

FIGS. 16A to 16E show the effects of I-5 hydrogel on axon growth and axon reinnervation, in which FIG. 16A shows images illustrating the NF positive axon growth and 5-HT axon growth in the FN-rich matrix in the transverse spinal cord sections at the epicenter of the lesion in animals injected with I-5 hydrogel; FIG. 16B shows an image illustrating the longitudinal spinal cord section from the group injected with I-5 hydrogel; FIG. 16C shows an image illustrating 5-HT axon innervations in the ventral motor regions of the lumbar spinal cord in sham-operated animals; and FIGS. 16D and 16E show graphs illustrating the quantification of 5-HT axon density in the ventral motor regions in the lumbar spinal cord.

BEST MODE

Figure 1:
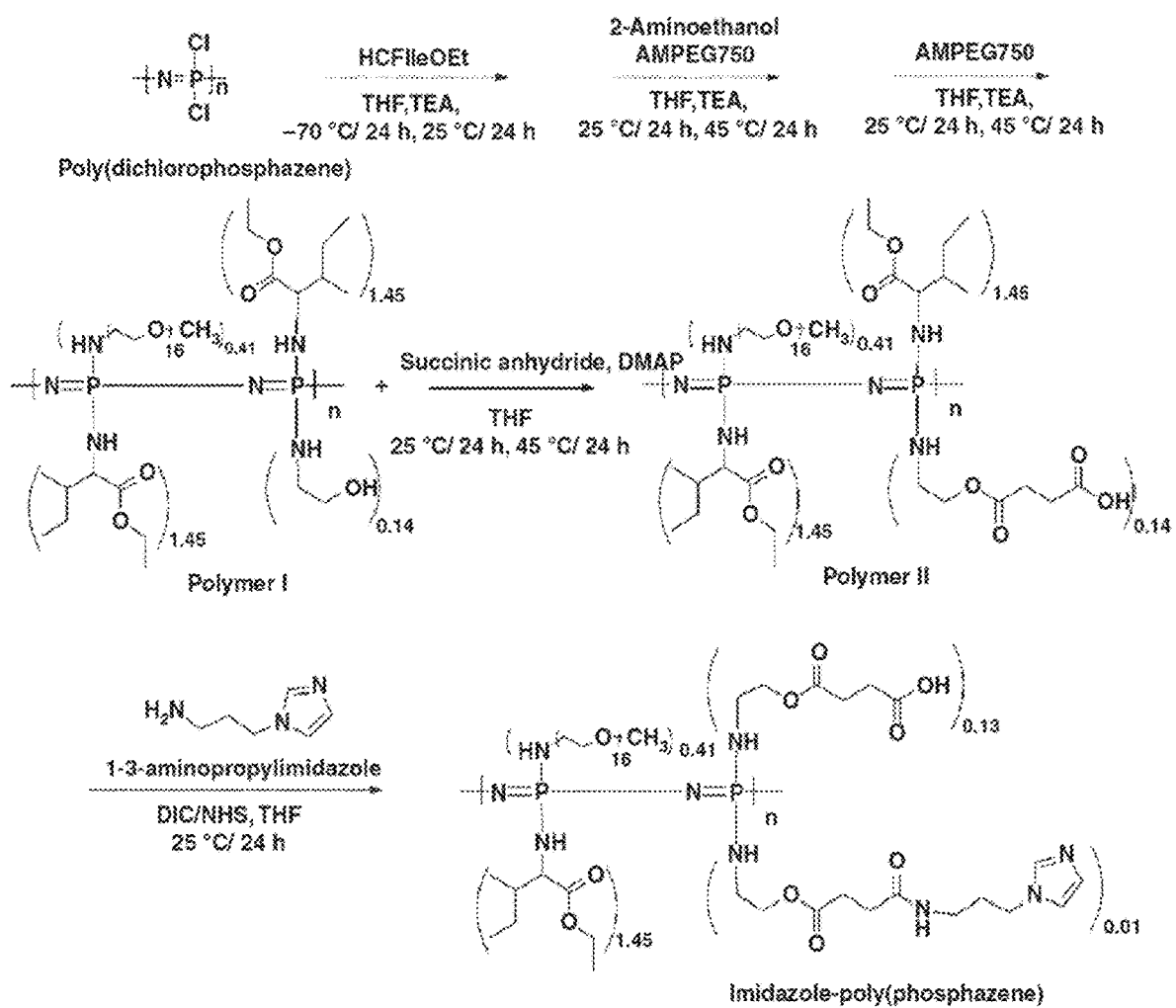
FIG. 1 shows a schematic diagram illustrating the synthesis of I-5.

An aspect of the present disclosure provides a pharmaceutical composition for preventing or treating spinal cord injury containing a compound of Formula 1 below or a pharmaceutically acceptable salt thereof.

simple method of injecting the compound of Formula 1 or pharmaceutically acceptable salt thereof into the spinal cord, and thereby spinal cord injury can be treated. In addition, the use of the above material was first confirmed in the present disclosure. In particular, the cystic spaces can be removed by filling the cystic cavities via single administration of the compound of Formula 1 or pharmaceutically acceptable salt thereof, not requiring combined administration with other cells or proteins.

In a specific embodiment, the compound of Formula 1 or pharmaceutically acceptable salt thereof may be able to treat spinal cord injury without the administration of additional cells or proteins.

The treatment of spinal cord injury with the composition for preventing or treating spinal cord injury composition or the compound of Formula 1 or pharmaceutically acceptable salt thereof of the present disclosure may be achieved by removing cystic cavities. As these materials promote regeneration of fibronectin-rich ECM and thus result in bridging, cystic cavities can thereby be filled. Specifically, ECM remodeling may be mediated by the activation of matrix

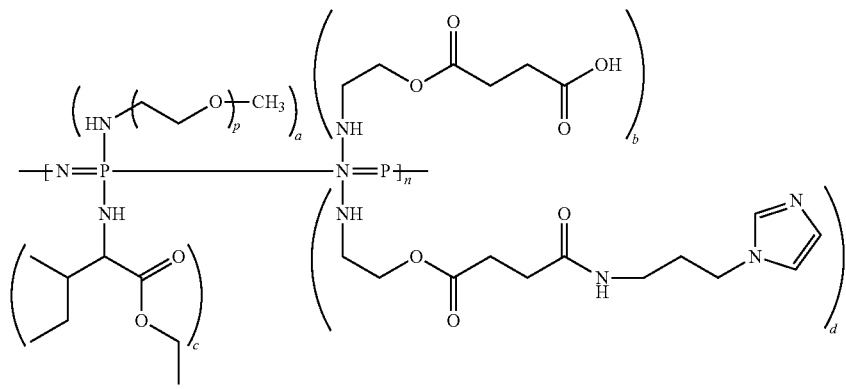

[Formula 1]

In Formula 1 above, p is in a range of 16 to 50, a, b, c, and d are values representing the amount of each substituent, which are each in a range of 0.01 to 1.9, the sum of (a+b+c+d) is 2, and n is a polymerization degree of polyphosphazene, which is in a range of 5 to 100,000.

In Formula 1 above, the p may be an integer.

Another aspect of the present disclosure provides a method for treating spinal cord injury which includes administering the compound of Formula 1 above or pharmaceutically acceptable salt thereof to a subject in need thereof.

In an embodiment, the compound of Formula 1 of the present disclosure may be one in which p is 16, a is 0.41, b is 0.13, c is 1.45, and d is 0.01, but the compound is not limited thereto.

In an embodiment, the compound of Formula 1 of the present disclosure may be an imidazole-poly(organophosphazenes) hydrogel, but the compound is not limited thereto.

In the present disclosure, the pathway for obtaining the compound is not particularly limited, and the compound may be chemically synthesized by a method known in the art, or a commercially available material may be purchased and used.

The present disclosure is based on the technical assumption that cystic cavities in the spinal cord can be filled via a metalloproteinase-9 (MMP-9) expressed in macrophages within the fibrotic ECM. The MMP-9 is a zinc-dependent endopeptidase capable of modulating ECM proteins. The MMP-9 with gelatinase activity can promote ECM remodeling and thus has a beneficial role in wound healing. This can be achieved by increasing the expression of MMP-9 gene.

The compound of Formula 1 or pharmaceutically acceptable salt thereof to be contained in the composition of the present disclosure, or the compound of Formula 1 or pharmaceutically acceptable salt thereof to be administered to subjects has an imidazole ring structure, which is a major residue of histamine. Macrophages are major cells which have a role in recruiting perivascular fibroblasts and triggering ECM remodeling and thereby healing cystic cavities and repairing tissue defects, and they express two types of histamine receptors, H1R and H4R42. The compound of Formula 1 includes an imidazole ring structure and thus interacts with histamine receptors via the imidazole ring structure. Accordingly, the interaction between the compound of Formula 1 and macrophages can activate MMP-9 and promote the remodeling of fibrotic ECM.

In an embodiment of the present disclosure, an experiment was performed to compare with a case where a polymer was injected which has physical properties similar to those of the compound of Formula 1 but no imidazole ring structure. As a result, it was confirmed that when a hydrogel without an imidazole ring was injected, the effect of the hydrogel in removing cystic cavities was not significant. That is, the compound of Formula 1 contained in the composition of the present disclosure can promote macrophage-mediated wound healing responses by dynamic interaction with macrophages, and can subsequently activate remodeling of fibrotic ECM and remove cystic cavities, thereby exhibiting the effect of treating spinal cord injury.

As used herein, the term "spinal cord injury (SCI)" refers to various kinds of damage to the spinal cord that occur when an external force is applied thereto. For example, the spinal cord injury may include clinical conditions representing the paralysis of peripheral motor muscles and sensory and autonomic nervous system at a lower side of the injured area due to damage in the major spinal cord tissues caused by trauma (e.g., spinal dislocation-fracture due to traffic accidents, fall from a height, etc.). Injuries to the spinal cord often result in vertebra, nerve, and blood vessel damage. Bleeding and the accumulation of fluids and swelling may occur inside or outside the spinal cord, but only within the vertebral canal. Pressure from the surrounding bones and meningeal structures may further damage the spinal cord. Additionally, edema of the spinal cord itself may additionally accelerate the loss of secondary tissues. A primary mechanical injury can initiate a cascade of secondary injury mechanisms, which includes accumulation of excessive excitatory neurotransmitters; formation of edema; movement of electrolytes (e.g., an increase of intracellular calcium); production of free radicals, especially oxidant-free radicals; production of eicosanoids; etc., and thus spinal cord injury may be considered as a two-step process. The primary injury results from shock, compression, or some other injury to the spinal cord, and the secondary injury is cellular and biochemical, wherein a cellular/molecular response can cause tissue destruction. Healing can be accelerated by blocking the secondary process and diffusing any compression resulting from the primary mechanical lesion as well as any spinal cord edema.

In the present disclosure, the spinal cord injury may be at least one selected from the group consisting of flexion injury, vertical compression injury, hyperextension injury, flexion rotation injury, acute transverse myelitis, acute disseminated encephalomyelitis, myelopathy, non-Hodgkin's lymphoma, hydrocephalus, hereditary ataxia, neurosyphilis, Minamata disease, amyotrophic lateral sclerosis, and multiple sclerosis, but the spinal cord injury is not limited thereto. In the present disclosure, the spinal cord injury may be any disease, without limitation, that can be treated or ameliorated by removal of cystic cavities and/or acceleration of ECM regeneration.

As used herein, the term "prevention" refers to all activities that suppress or delay the onset, spread, and recurrence of spinal cord injury by administration of the pharmaceutical composition of the present disclosure, and the term "treatment" refers to all activities that improve or advantageously change the symptoms of spinal cord injury by administration of the pharmaceutical composition of the present disclosure.

In a specific embodiment, the treatment of spinal cord injury may be to ameliorate spinal cord injury.

The pharmaceutical composition of the present disclosure may be used as a single agent, or may be prepared and used as a combination preparation by further including a certified pharmaceutical composition, which is known to have an effect of preventing or treating spinal cord injury. The pharmaceutical composition of the present disclosure may be formulated in the form of a pharmaceutical unit dose by further including a pharmaceutically acceptable carrier, excipient, or diluent. The pharmaceutical acceptable carrier, excipient, or dilute may be a non-naturally occurring material or naturally occurring material, but is not limited thereto. As used herein, the term "pharmaceutically acceptable" refers to a property which neither excessively stimulates a bioorganism nor inhibits the biological activity and properties of an active material to be administered.

The compound of Formula 1 or pharmaceutically acceptable salt thereof to be administered to a subject may further include a component that is included in the pharmaceutical composition.

Additionally, in a specific embodiment, the administration may be to administer a composition which contains the compound of Formula 1 or pharmaceutically acceptable salt thereof.

In the present disclosure, the pharmaceutical composition containing a pharmaceutically acceptable carrier may be prepared in any formulation type selected from the group consisting of tablets, pills, powders, granules, capsules, suspensions, liquid medicine for internal use, emulsions, syrups, sterile aqueous solutions, non-aqueous solvents, lyophilized preparations, and suppositories.

The composition of the present disclosure or the compound of Formula 1 or pharmaceutically acceptable salt thereof may further include pharmaceutically acceptable carriers, diluents, or excipients, and these additives may be prepared in various formulation types including those for oral administration (e.g., powders, granules, tablets, capsules, suspensions, emulsions, syrups, aerosols, etc.); injections of sterile injection solutions; etc. according to the conventional methods to be suitable for each intended purpose of use. The composition of the present disclosure or the compound of Formula 1 or pharmaceutically acceptable salt thereof may be administered via oral administration or various routes including intravenous, intraperitoneal, subcutaneous, rectal, and topical administration. Examples of suitable carriers, excipients, or diluents that can be contained in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition of the present disclosure may further contain a filler, anti-coagulant, lubricant, humectant, fragrance, preservative, etc.

The pharmaceutical composition or the compound of Formula 1 or pharmaceutically acceptable salt thereof may be prepared in various formulation types. The formulations may be prepared using a commonly used diluent or excipient (e.g., a filler, an extender, a binder, a humectant, a disintegrant, a surfactant, etc.).

Solid formulations for oral administration may include tablets, pills, powders, granules, capsules, etc., and these solid formulations may be prepared by adding at least one excipient (e.g., starch, calcium carbonate, sucrose or lactose, gelatin, etc.). Additionally, a lubricant (e.g., magnesium stearate, talc, etc.) may be used, in addition to the simple excipient. Liquid formulations for oral administration may include suspensions, liquid medicines for internal use, emulsions, syrups, etc., and various excipients (e.g., humectants, sweeteners, fragrances, preservatives, etc.) may be used, in addition to the simple diluents (i.e., water and liquid paraffin).

Formulations for parenteral administration may include sterile aqueous solutions, non-aqueous solvents, suspensions, emulsions, lyophilized preparations, suppositories, etc. Examples of the non-aqueous solvents and suspensions may include vegetable oils (e.g., propylene glycol, polyethylene glycol, and olive oil), injectable esters (e.g., ethyl oleate, etc.). Examples of the bases for suppositories may include Witepsol, macrogol, Tween 61, cacao butter, laurinum, glycerogelatin, etc.

In the composition of the present disclosure, the compound of Formula 1 or pharmaceutically acceptable salt thereof may be administered in a pharmaceutically effective amount. As used herein, the term "pharmaceutically effective amount" refers to an amount sufficient for the treatment of diseases at a reasonable benefit/risk ratio applicable to medical treatment without causing any side effects, and the level of the effective dose may be determined based on the factors including the health status of a patient, type of a disease, severity of illness, drug activity, drug sensitivity, administration method, administration time, administration route and dissolution rate, length of treatment, factors including a drug to be used simultaneously in combination, and other factors well known in the medical field. The composition of the present disclosure may be administered as an individual therapeutic agent, in combination with another therapeutic agent, or sequentially or simultaneously with a conventional therapeutic agent, and may be administered once or multiple times. It is important to administer the pharmaceutical composition in an amount to obtain the maximum effect with a minimum amount without adverse effects considering all of the factors described above, and the pharmaceutically effective amount can easily be determined by one of ordinary skill in the art.

Still another aspect of the present disclosure provides a method for preventing or treating spinal cord injury which includes administering the pharmaceutical composition to a subject in need thereof.

The terms "pharmaceutical composition", "spinal cord injury", "prevention", and "treatment" are as described above.

tion of the present disclosure can exhibit a synergistic effect by administration in combination with a conventional therapeutic agent.

As used herein, the term "administration" refers to the introduction of a particular material into a patient by any appropriate method, and the composition containing the compound of Formula 1 of the present disclosure or a pharmaceutically acceptable salt thereof may be administered by any conventional administration route that enables delivery of the composition to the target tissue. The administration route may include intraperitoneal administration, intravenous administration, intramuscular administration, subcutaneous administration, intradermal administration, oral administration, topical administration, intranasal administration, intrapulmonary administration, intrarectal administration, etc., but the administration route is not limited thereto. Additionally, the pharmaceutical composition of the present disclosure may be administered using any device capable of transporting active ingredients into a target cell. The preferred methods of administration and preparations are intravenous, subcutaneous, intradermal, intramuscular, drop injections, etc. The injections may be prepared using aqueous solvents (e.g., physiological saline, Ringer's solution, etc.) and non-aqueous solvents (e.g., vegetable oils, higher fatty acid esters (e.g., ethyl oleate, etc.), alcohols (e.g., ethanol, benzyl alcohol, propylene glycol, glycerin, etc.)), etc. The injections may include a pharmaceutical carrier (e.g., stabilizers for preventing deterioration (e.g., ascorbic acid, sodium bisulfite, sodium metabisulfite, BHA, tocopherol, EDTA, etc.), emulsifiers, buffers for pH control, preservatives for inhibiting the growth of microorganisms (e.g., phenylmercuric nitrate, thimerosal, benzalkonium chloride, phenol, cresol, benzyl alcohol, etc.).

Still another aspect of the present disclosure provides a food composition for preventing or ameliorating spinal cord injury, which contains the compound of Formula 1 below or a sitologically acceptable salt thereof

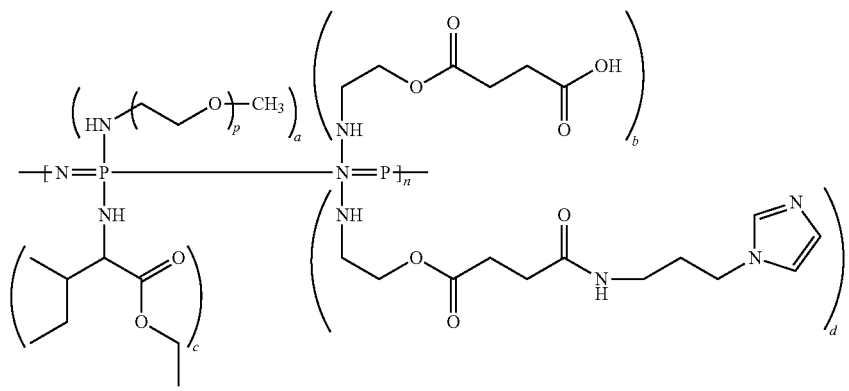

[Formula 1]

As used herein, the term "subject" refers to all kinds of animals including humans (e.g., monkeys, cattle, horses, sheep, pigs, chickens, turkeys, quails, cats, dogs, mice, rats, rabbits, guinea pigs, etc.) suspected of having spinal cord injury or at risk of developing spinal cord injury. Spinal cord injury can be prevented or treated by administering the composition of the present disclosure or the compound of Formula 1 or pharmaceutically acceptable salt thereof to the above subjects. Additionally, the pharmaceutical composi- In Formula 1 above, p is in a range of 16 to 50, a, b, c, and d are values representing the amount of each substituent, which are each in a range of 0.01 to 1.9, the sum of (a+b+c+d) is 2, and n is a polymerization degree of polyphosphazene, which is in a range of 5 to 100,000.

The terms "compound of Formula 1", "pharmaceutical composition", "spinal cord injury", and "prevention" are as described above.

In the present disclosure, the compound of Formula 1 may be present in the form of a pharmaceutically or sitologically acceptable salt.

As used herein, these terms (i.e., "pharmaceutically acceptable salt" and "sitologically acceptable salt") refer to any and all organic or inorganic addition salts of the compound of Formula 1 at a concentration relatively non-toxic and harmless to a patient with a beneficial effect, in which side effects of the compound of Formula 1 based on these salts do not deteriorate the beneficial effect of the compound. Any such organic or inorganic addition salt may be used without limitation as long as it shows activity equivalent to that of the compound of Formula 1.

Acid addition salts may be prepared by a convention method, for example, by dissolving a compound in an excess amount of an aqueous acid solution followed by precipitating the resulting salt using a water-miscible organic solvent (e.g., methanol, ethanol, acetone, or acetonitrile). An equimolar amount of the compound and the acid or alcohol in water (e.g., glycol monomethyl ether) may be heated, and subsequently, the mixture may be evaporated and dried, or the precipitated salt may be subjected to suction filtration.

As a free acid, both organic and inorganic acids can be used, for example, inorganic acids such as hydrochloric acid, phosphoric acid, sulfuric acid, nitric acid, etc., and organic acids such as methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc., but the free acid is not limited thereto.

Additionally, a pharmaceutically acceptable metal salt may be prepared using a base. An alkali metal salt or alkali earth metal salt may be prepared, for example, by dissolving a compound in an excess amount of an alkali metal hydroxide or alkali earth metal hydroxide solution, filtering the non-dissolved compound salt, and evaporating the filtrate, followed by drying. In particular, examples of the pharmaceutically acceptable metal salt may include sodium, potassium, or calcium salts, but the pharmaceutically acceptable metal salt is not limited thereto. Additionally, a corresponding silver salt may be prepared by reacting an alkali metal or alkali earth metal salt with an appropriate silver salt (e.g., silver nitrate).

The pharmaceutically acceptable salt of the compound of the present disclosure may include salts of an acidic or basic group that can be present in the compound of Formula 1, unless otherwise instructed. For example, the pharmaceutically acceptable salt may include sodium, calcium, or potassium salts of a hydroxy group, etc., and other pharmaceutically acceptable salts of an amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc., and may be prepared by a salt preparation method known in the art.

Still another aspect of the present disclosure provides a method for removing cystic cavities in the spinal cord, which includes administering the compound of Formula 1 above or pharmaceutically acceptable salt thereof to a subject in need thereof.

The terms "compound of Formula 1", "spinal cord injury", and "removal of cystic cavities in the spinal cord" are as described above.

DETAILED DESCRIPTION OF THE INVENTION

Hereinafter, the present disclosure will be described in detail through exemplary embodiments. However, these exemplary embodiments are for illustrative purposes only and are not intended to limit the scope of the present disclosure.

Preparation Example 1

Synthesis of Imidazole-Poly(Organophosphazene) Hydrogel

All reactions were conducted in a dry nitrogen atmosphere using standard Schlenk-line techniques. The imidazole-poly(organophosphazene) hydrogel of the present disclosure was synthesized according to the process shown in FIG. 1.

Step 1: Synthesis of $[NP(IleOEt)_{1.45}(AEtOH)_{0.14}(AMPEG750)_{0.41}]_n$ (Polymer I, EP)

IleOEt·HCl (23.81 g, 121.67 mmol) in dry tetrahydrofuran (THF) containing triethylamine (TEA) was added slowly to poly(dichlorophosphazene) (10.00 g, 86.29 mmol) dissolved in dry THF. The reaction mixture was incubated in a dry ice bath for 12 hours and at room temperature for 36 hours. AEtOH (1.56 g, 25.50 mmol) and AMPEG750 (37.53 g, 50.04 mmol) were dissolved in dry THF containing TEA and added to the mixture. The reaction mixture was stirred at room temperature for 24 hours and then at 40° C. to 50° C. for 24 hours. AMPEG750 (18.76 g, 25.02 mmol) in the dried THF was added to the reaction mixture and stirred at room temperature for 24 hours and then at 40° C. to 50° C. for 24 hours. The reaction mixture was filtered and the filtrate was concentrated and poured into n-hexane to obtain a precipitate, which was re-precipitated twice in the same solvent system. The polymer product was purified by dialysis with a dialysis membrane (Spectra/Por®, Molecular Weight Cut-Off (MWCO): 10 kDa to 12 kDa) against methanol at room temperature for 4 days and against distilled water at 4° C. for 4 days. The dialyzed solution was freeze-dried to obtain Polymer I.

Yield: 82%

$^1$H NMR (CDCl$_3$), δ (ppm): 0.8-1.0 (s, 6H), 1.1-1.3 (b, 3H), 1.3-1.6 (b, 2H), 1.6-1.9 (b, 1H), 2.8-3.3 (b, 2H), 3.4-3.8 (b, 73H), 3.9 (s, 1H), 4.0-4.3 (b, 3H).

Step 2: Synthesis of $[NP(IleOEt)_{1.45}(Succinic\ acid)_{0.14}(AMPEG750)_{0.41}]_n$ (Polymer II, CP-2)

Succinic anhydride (2.76 g, 27.58 mmol) and 4-(dimethylamino)pyridine (DMAP) (3.37 g, 27.56 mmol) dissolved in dry THF, were added separately into Polymer I (27.12 g, 45.94 mmol) in dry THF. The reaction mixture was stirred at 40° C. for 24 hours. The products were dialyzed with a dialysis membrane (Spectra/Por®, MWCO: 10 kDa to 12 kDa) against methanol at room temperature for 4 days and against distilled water at 4° C. for 4 days. The dialyzed solution was freeze-dried to obtain Polymer II.

Yield: 91%

$^1$H NMR (CDCl$_3$), δ (ppm): 0.8-1.0 (s, 6H), 1.1-1.3 (b, 3H), 1.3-1.6 (b, 2H), 1.6-1.9 (b, 1H), 2.5-2.8 (b, 2H), 2.8-3.3 (b, 2H), 3.4-3.8 (b, 62H), 3.9 (s, 1H), 4.0-4.3 (b, 3H).

Step 3: Synthesis of [NP(IleOEt)$_{1.45}$(Succinic Acid)$_{0.13}$(Imi)(AMPEG750)$_{0.41}$] (I-5)

Carboxylic acid-terminated Polymer II (10 g, 16.55 mmol) was dissolved in dry THF. After cooling to 0° C., diisopropylcarbodiimide (DIC; 3.58 mL, 23.17 mmol) and N-hydroxysuccinimide (NHS; 2.67 g, 23.16 mmol) were added, and the mixture was stirred for 30 minutes in order to activate the carboxyl groups of the polymer. The mixture was moved to 1-(3-aminopropyl)imidazole (1.45 g, 11.54 mmol) dissolved in distilled THF. The reaction mixture was stirred at 0° C. for 6 hours and then at room temperature for 18 hours. Then, the solution was concentrated and purified by precipitation with a 1 M potassium fluoride solution. The precipitate was dialyzed with a dialysis membrane (Spectra/Por®, Spectrum Laboratories, MWCO: 12 kDa to 14 kDa) against distilled water at 4° C. for 3 days, and the dialyzed solution was freeze-dried to obtain the final product (I-5).
Yield: 79%
$^1$H NMR (CDCl$_3$), δ (ppm): 0.8-1.0 (s, 6H), 1.1-1.3 (b, 3H), 1.3-1.6 (b, 2H), 1.6-1.9 (b, 1H), 2.5-2.8 (b, 4H), 2.6-2.9 (b, 49H), 2.8-3.3 (b, 2H), 3.4-3.8 (b, 75H), 3.9 (s, 1H), 4.0-4.3 (b, 5H), 6.9-7.2 (b, 1H), 7.4-7.6 (b, 1H), 7.9-8.1 (s, 1H).

Preparation Example 2

Preparation of I-5 Hydrogel Solution 10 wt % of the I-5 polymer in PBS solution was used for experiments after filtration using a cellulose acetate syringe filter (0.2 μm). In the experiments where the I-5 polymer solution was mixed with Taxol® or siRNA nanoparticles, the I-5 solution (20 wt %) was prepared and used.

Experimental Method 1

Measurement of Physical Properties

The structures of the polymers prepared in Examples above were estimated by a $^1$H-NMR spectrometer (Varian Gemini-300, Agilent Technologies) operating at 400 MHz in the Fourier transform mode using CDCl$_3$ as a solvent and by an FT-IR spectrometer (Spectrum GX FT-IR, Perkin-Elmer). The amount of substituted imidazole groups in IP was determined by BCA assay (Pierce). The conjugation of imidazole was confirmed by a high-performance liquid chromatography (HPLC) system (Agilent, 1050 series).

The molecular weight of the I-5 was calculated using a gel permeation chromatography system (Waters 1515, Waters) including a refractive index detector (Waters 2410) and two Styragel® columns (Waters Styragel HR 4E and HR 5E) connected in line at 35° C. at a flow rate of 1 mL/min. THF containing 0.1 wt % tetrabutylammonium bromide was used as a mobile phase. Polystyrenes (MW: 1,270; 3,760; 12,900; 28,400; 64,200; 183,000; 658,000; 1,050,000; 2,510,000; and 3,790,000) were used as standards.

The viscosity of the aqueous I-5 hydrogel was measured over a wide temperature range. Specifically, the viscosity of the aqueous I-5 hydrogel solution was measured using a Brookfield RVDV-III+ viscometer (Brookfield) between 5° C. and 70° C. under a fixed shear rate of 0.1 s$^{-1}$. The viscosity was measured with a set spindle speed of 0.2 rpm at a heating rate of 0.33° C./min.

For the in vitro stability test, 10% polymer solutions were mixed with a fluorescence dye, Rhodamine B (100 μL), and 200 μL of each labeled polymer solution was loaded onto millicells (pore size: 12.0 μm). The millicells containing polymer solutions were incubated for 30 minutes in a 37° C. heated oven. Then, the millicells were transferred to each glass tube containing 3 mL of PBS, and the tube was cultured in a shaking incubator maintained at 37° C.

Experimental Method 2

Evaluation of Biocompatibility

For evaluation of in vitro cytotoxicity, NIH3T3 cells were seeded in 96-well tissue culture plates at a density of 1×10$^4$ cells/well. After incubation for 24 hours, the cells were washed with PBS. Then, 0.2 mL of the polymer solution was added to each well and the plates were incubated at 37° C. in a humidified atmosphere with 5% CO$_2$ for 24 hours. Cell viability was measured using the EZ-CYTOX assay kit (Dogen Bio) following the manufacturer's instructions. The absorbance was determined at a wavelength of 450 nm using a microplate reader (Molecular Devices).

For in vivo biocompatibility testing, 100 μL of 10 wt % was injected into the dorsal subcutis of BALB/c mice (6 weeks old, female). Body weight was monitored for 28 days and the existence of inflammatory signs in the tissue was examined at predetermined time points.

Experimental Method 3

Animals and Surgical Procedures

All animal protocols were approved by the Institutional Animal Care and Use Committee of Ajou University School of Medicine. Adult female Sprague Dawley rats (250 g to 300 g) were used in this study.

Spinal contusion injury was inflicted using the Infinite Horizon impactor (Precision Systems and Instrumentation). Animals were anesthetized with 4% chloral hydrate (10 mL/kg, injected intraperitoneally), followed by a dorsal laminectomy at the 10$^{th}$ thoracic vertebral level (T10 to T11) to expose the dorsal surface of the spinal cord. Then, standardized contusion at a force of 200 kdyn was performed with the Infinite Horizon impactor. After the injury, muscles were sutured in layers and the skin was stapled. Bladder care was provided twice daily until spontaneous voiding resumed. I-5 injection was performed 1 week after contusion injury to avoid potential tissue damage related to the injection itself. I-5 hydrogel solution (10%) was maintained on ice until it was loaded into a 26G Hamilton syringe (Model: 701RN) to prevent gelation. The rats were anesthetized and the dorsal surface of the spinal cord with the previous contusion injury was re-exposed. After the contused area was identified under bright illumination, the Hamilton syringe was advanced into the center of the contused area and 10 μL of the I-5 solution was injected manually. After injection, the syringe was kept in situ for 1 minute to prevent regurgitation of the injected hydrogel through the injection site.

When I-5 was injected with Taxol (1 μg/μL) or siRNA nanoparticles (see the section below), equal volumes of the agent and a 20 wt % solution of I-5 were mixed, yielding a final gel concentration of 10 wt %. For injection of AAV8-GFP for anterograde tracing of corticospinal axons, rats were placed on a stereotaxic frame, and a midline incision was made over the skull to expose the bregma. The skull overlying the right sensorimotor cortex was removed using a microdrill, and the AAV virus (AAV8 serotype with UbC promoter expressing GFP) was injected into the cortex through a 10 μL Hamilton microsyringe tipped with a pulled glass micropipette attached to a nanoliter injector. Ten injections (100 nL per site) were performed at a rate of 50 nL/min at the following coordinates: 1.5 mm and 2.0 mm lateral; 0.7 mm deep; 1.0 mm and 1.5 mm anterior; 0.3 mm, 0.8 mm, and 1.3 mm posterior to the bregma. For BDA injection, a midline incision was made over the thoracic vertebrae and a laminectomy was performed to expose the underlying T6 to T7 spinal cord and 10% BDA (10,000 MW; D1956, Invitrogen) tracer was injected into the right ventral gray matter (500 nL per site) using the following coordinates; 0.6 mm lateral; depth, 1.5 mm and 2 mm. The needle was left in place for 1 minute before moving to the next site. The brain and spinal cord were kept moist during the procedure and the skin was closed with sutures. The rats were sacrificed three weeks after external tracer injections.

Experimental Method 4

Knockdown of MMP-9 by siRNA Nanoparticles

To determine whether MMP-9 mediates the fibrotic ECM remodeling induced by I-5 hydrogel, the present inventors have performed a knockdown experiment using MMP-9 siRNA delivered by nanoparticles.

To knockdown MMP-9 in vivo spinal cord tissue, the present inventors have used lipid nanoparticle-mediated siRNA delivery technology (Precision Nanosystems). Specifically, fluorescently labeled SUB9KITS™ nanoparticles were conjugated with candidate siRNA molecules with sequences targeting MMP-9. Validation of siRNA-mediated knockdown was performed using rat peritoneal macrophages. A total of $1 \times 10^5$ peritoneal macrophages were plated per well in a 24-well plate. After incubation for 24 hours, the medium was removed and the cells were cultured with 1 μg/mL siRNA-nanoparticles for 2 days. Total RNA was extracted using a PureLink™ RNA Mini Kit (Ambion) according to the manufacturer's instructions. cDNA was synthesized from 500 ng of total RNA using oligo dT primers and a PrimeScript™ $1^{st}$ strand cDNA Synthesis Kit (Takara). Real-time quantitative PCR was performed using SYBR Premix Ex Taq in an ABI 7500 system (Applied Biosystems). MMP-9 (NCBI: NM_031055) primers were designed as follows: forward: 5'-GGCCTATTTCTGCCAT-GACAAATAC-3' (SEQ ID NO:1) and reverse: 5'-CTG-CACCGCTGAAGCAAAAG-3' (SEQ ID NO:2) (expected product size: 141 bp). The primers for ribosomal RNA used as a loading control were as follows: forward: 5'-CGCG-GTTCTATTTTGTTGGT-3' (SEQ ID NO:3) and reverse: 5'-AGTCGGCATCGTTTATGGTC-3' (SEQ ID NO:4) (expected product size: 240 bp).

MMP-9 knockdown was also validated using immunocytochemistry. After two days of incubation with 2 μg/mL siRNA nanoparticles, peritoneal macrophages were fixed and the cells were stained with rabbit MMP-9 antibody (1:100; Millipore). For in vivo delivery, siRNA was re-encapsulated with lipid nanoparticles to produce highly concentrated siRNA-nanoparticles. For injection, 5 μL of 5 mg/mL nanoparticles were mixed with 5 μL of 20% I-5 hydrogel.

Experimental Method 5

Tissue Processing and Histochemistry

For histological assessment of the lesion sites, rats were sacrificed at early time points (1 week after injection or 2 weeks after injury) and late time points (4 weeks after injection or 5 weeks after injury). Specifically, the rats were deeply anesthetized with chloral hydrate and perfused intracardially with PBS, followed by 4% paraformaldehyde in 0.1 M phosphate buffer at pH 7.4. Then, the spinal cord was dissected and tissue blocks were inoculated with 4% paraformaldehyde for 2 hours and then cryoprotected in a graded series of sucrose solutions. 20 μm-thick sections of the spinal cord were cut transversely using a cryostat (CM 1900; Leica) and thaw-mounted onto Super Frost Plus slides (Fisher Scientific).

For morphological assessment of lesion sites, serial spinal cord sections were stained with eosin and eriochrome. The spinal cord sections were immersed in a staining solution consisting of 240 mL of 0.2% eriochrome cyanine (RC; Sigma) and 10 mL of 10% $FeCl_3.6H_2O$ (Sigma) in 3% HCl for 8 minutes. After washing under flowing tap water, the sections were differentiated with 1% $NH_4OH$. After staining with eriochrome cyanine, the sections were contrast-stained with eosin solution for improved visualization of the lesion sites.

For immunohistochemistry, spinal cord tissue sections were incubated overnight at 4° C. with primary antibodies: anti-GFAP (1:500; Dako, #0334), anti-fibronectin (1:100; Sigma, # F36480), Iba-1 (1:500; Wako, #019-19741), anti-PDGFR-β (1:300; Abcam), anti-collagen 1α1 (1:100; Santa Cruz, # sc-8784), anti-5-HT (5-hydroxytryptamine; 1:5000; Immunostar, #20080), anti-MMP-9, (1:100; Millipore, # AB19016), anti-CD45 (1:500; Bio-Rad, # MCA589R), ant-MBP (1:200; Abcam, # ab7399), CD206 (1:500; Abcam, # ab64693), or anti-CD11b (1:500; Bio-Rad, # MCA275R). After washing three times, the slides were incubated with appropriate secondary antibodies conjugated to the Alexa Fluor fluorescent dyes. For BDA staining, Alexa Fluor® 594-conjuaged Streptavidin (1:500; Molecular Probes, # S32356) was used. Images were captured using a confocal laser-scanning microscope (Olympus). For brightfield imaging of GFAP immunoreactivities, spinal cord sections were incubated with anti-GFAP (1:2000; Dako, #0334) followed by biotinylated goat anti-rabbit IgG secondary antibody (1:400), and the antigen-antibody reaction was visualized using a Vectastain Elite ABC kit (Vector) with a Vector SG peroxidase substrate kit (Vector).

Tissue clearing and LFSM imaging of whole spinal cord tissue were performed as described above. Meninges of injured spinal cord were carefully removed and an 8 mm length of the spinal cord tissue centered on the epicenter region was cut. The samples were dehydrated in 50%, 80%, and 100% tetrahydrofuran (THF) solutions on an agitating incubator at RT each for 3 hours and finally switched to fresh 100% THF overnight. Next, THF solutions were switched to benzyl alcohol and benzyl benzoate (BABB), and the spinal cord tissue samples were continuously incubated on an agitating incubator until they became transparent. After tissue clearing, longitudinal images of the spinal cord tissue samples were taken by LSFM (Ultramicroscope, Lavision Biotec) at a 12.5× magnification with a 3 μm inter-image thickness. Based on autofluorescence signals from the spinal cord tissue, it was possible to delineate cystic spaces devoid of the tissue from the residual spinal cord. The boundaries of cystic cavities were manually drawn in every third image and the cystic cavities were highlighted in magenta.

Experimental Method 6

Three-Dimensional Reconstruction and Quantitative Image Analysis

For quantitative analysis of cavity volume, serial spinal cord sections stained with eriochrome and eosin were threedimensionally reconstructed. Three-dimensional reconstruction of the lesion cavity was performed using the Neurolucida software equipped with the 3D Slide Scanning Module (MBF bioscience). A total of 24 serial transverse spinal cord sections equally spaced 400 μm apart were used to create a 3D image corresponding to a 1 cm-long spinal cord segment. Contours of the spinal cord outer boundary, the white matter, the cystic cavity, the intact gray matter, and the pathological spinal cord tissue (the area in which normal tissue architecture was not maintained) were manually drawn on each section, and then 3D images were generated by the Virtual Tissue software program, in which different colors were assigned to distinguish the white matter (light gray), the gray matter (green), the pathologic spinal cord tissue (yellow), and the cystic cavity (red).

Additionally, the volumes of the cystic cavities were automatically calculated using the Neurolucida software. To examine the possibility that I-5 may induce inflammatory reactions in the spinal cord tissue, the present inventors have examined the intensity of immunoreactivity for Iba1, a marker of inflammatory macrophages. For quantification of Iba1-immunoreactive signal intensity, three regions of interest (ROIs) of identical size were placed at the dorsal, lateral, and ventral regions containing the borders between the residual white matter and damaged tissue regardless of cavities at the epicenter. A lateral border of the dorsal ROI was placed immediately medial to the dorsal horn so that the dorsal ROI was located on the dorsal column. A lateral ROI was located just above the line crossing the intermediolateral horn. When the intermediolateral horn could not be identified due to the lesion, the lower border of the lateral ROI was placed just above the transverse midline of the spinal cord section. A ventral ROI was located below the ventral horn. When the ventral horn could not be located due to the lesion, the medial border of the ventral horn was placed 500 μm apart from the vertical midline of the spinal cord section. Then, the Iba1-immunoreactive signal above the predetermined threshold value was quantified using the ImageJ software (publicly available at http://imagej.nih.gov/ij/).

To examine potential mechanisms by which I-5 injection enhances functional outcomes, the number of surviving motor neurons in the ventral horns caudal to the injury epicenter was analyzed 8 weeks after injury. For quantification of the number of motor neurons below the lesion site, pairs of transverse spinal cord sections (with an intersection interval of 40 μm) were selected 1.2 mm, 1.6 mm, and 2.0 mm caudal to the epicenter. The sections were stained with eriochrome and cresyl violet, and the surviving motor neurons with the longest cell diameter of at least 20 μm were identified and counted using a bright field microscope (Olympus BX51). The average number of motor neurons in each pair was calculated.

For quantification of MBP immunoreactivity in the residual white matter, transverse sections 2 mm rostral to the epicenter, at the epicenter, and 2 mm caudal to the epicenter were selected and stained with anti-MBP antibodies. Three ROIs of identical size were placed in the dorsal, lateral, and ventral white matter regions. The ROIs were located using the same criteria as described above for quantification of Iba1-immunoreactive signal intensity. The only difference was that the ROIs were placed within the MBP-positive residual white matter. Then, the MBP-immunoreactive signal above the predetermined threshold value was quantified using the ImageJ software. The quantification of the 5-HT axon density in the caudal lumbar motor regions was performed as described above with slight modification. Two transverse sections located 10 mm and 13 mm caudal to the epicenter were obtained from each animal. The number of pixels in the ventral motor regions occupied by the 5-HT fibers was quantified using ImageJ, and these values were normalized to the number of 5-HT fiber pixels in ventral motor regions rostral to the epicenter.

Experimental Method 7

Zymography

The present inventors have confirmed whether certain matrix remodeling enzymes may be involved in the formation of fibrotic matrix after I-5 injection. MMPs are zinc-dependent endopeptidases capable of modulating ECM proteins, and MMPs with gelatinase activity have beneficial roles in matrix remodeling and wound healing.

For detection of MMP-2 and MMP-9 enzymatic activities, animals injected with PBS (N=5) and I-5 (N=4) were sacrificed 1 week after injection (2 weeks after injury). The 1 cm-long spinal cord segment with the epicenter at its center was dissected and quickly frozen at −70° C. The spinal cord tissue was homogenized and sonicated in RIPA buffer. 50 μg of the protein sample was loaded onto a polyacrylamide gel containing SDS and gelatin and subjected to electrophoresis. The gel was re-natured in a buffer (2.5% Triton X-100) to allow proteins to regain their enzymatic activities, and then washed 3 times with a developing buffer containing 50 mM Tris-HCl, 200 mM NaCl, 5 μM $ZnCl_2$, 5 mM $CaCl_2$, and 0.2% Brij-35 (Sigma). The gel was transferred to a fresh developing buffer and incubated at 37° C. for 72 hours. Then, the gel was stained with Coomassie blue for 2 hours followed by destaining in methanol and formic acid. The intensity of clear bands resulting from protease digestion was determined by densitometry using the ImageJ software.

Experimental Method 8

In Vitro Assay for Interaction Between Macrophages and I-5

In the injured mouse spinal cord, hematogenous macrophages are closely associated with collagen 1α1-positive perivascular fibroblasts and have a role in recruiting fibroblasts and promoting regeneration of fibrotic matrix. The present inventors have generally confirmed that macrophages within the fibrotic matrix can induce recruitment of perivascular fibroblasts and ECM remodeling leading to formation of the fibrotic matrix. I-5 hydrogel contains an imidazole group, which is a major residue of histamine, and macrophages express two types of histamine receptor, H1R and H4R. Therefore, the present inventors have tested whether I-5 hydrogel physically interacts with macrophages through binding to their histamine receptors.

To visualize the interaction between the polymer hydrogel and macrophages in vitro, poly(organophosphazene) polymer solutions were mixed with the hydrophobic fluorescent dye Nile Red (Sigma-Aldrich). The hydrophobic interaction between the polymer and Nile Red induced the formation of nano-scaled polymer micelles emitting red fluorescence. When 80 μg of a polymer solution was mixed with 0.1 μg of Nile Red and sonicated for 1 hour, the mixture formed particulate micelle structures. The formation of nanoparticles made of polymer micelle structures was confirmed by a size increase after addition of Nile Red from 30 nm to 34 nm, as measured using a Zetananosizer (Zetasizer Nano ZS, Malvern Instruments Ltd.). RAW 264.7 cells (purchased from ATCC; ATCC® TIB-71™) were seeded in 24-well plates ($2.5 \times 10^4$ cells/well) and incubated overnight in complete DMEM culture medium. Then, the culture medium was replaced with 1 mL of serum-free medium containing the nanoparticles composed of Nile Red or polymer with or without the imidazole group. After 1 hour, 1 mL of complete medium was added to every well and the cells were incubated for 2 hours. After washing the cells with PBS, fluorescence images of the cultured macrophages were captured using a confocal microscope (Olympus). The intensity of Nile Red fluorescence was quantified using a fluorescence spectrophotometer (Synergy H1 Multi-mode).

To determine whether the interaction was mediated by histamine receptors, mepyramine maleate (Santa Cruz) (i.e., an inhibitor of histamine receptor 1 (H1)) or JNJ7777120 (Santa Cruz), (i.e., an inhibitor for histamine receptor 4 (H4)) was added at a concentration of 20 μM to cultured macrophage cells 30 minutes before adding the nanoparticles.

Experimental Method 9

Evaluation of Behavior

To assess functional recovery after injection with I-5 or PBS, Basso-Beattie-Bresnahan (BBB) open field locomotor scores were measured after injury (7 weeks after PBS or I-5 injection).

The number of animals required for behavioral analyses was determined based on the report on the BBB open field locomotor test where 5 to 9 animals per group were used (Basso, D. M., Beattie, M. S. & Bresnahan, J. C. Graded histological and locomotor outcomes after spinal cord contusion using the NYU weight-drop device versus transection. Exp. Neurol. 139, 244-256 (1996)). Animals that showed a BBB score of 3 or higher at one day after contusion injury were excluded. One subject in the PBS injection group and two subjects in the I-5 injection group were excluded. Immediately after contusion injury, animals were randomly allocated to either PBS (N=9) or I-5 hydrogel (N=8). To ensure blind assessment of behavioral recovery, the animals were assigned new identification codes after the injection 1 week after injury by an independent experimenter who was not involved in either animal surgery or behavioral assessment. The original identification codes had been available only to the independent experimenter until all of the behavioral experiments and assessments (including Catwalk analysis) were completed. Locomotor recovery was evaluated using the BBB open field locomotor scale and Catwalk footprint analysis (Noldus Information Technology). Rats were allowed to walk freely in an open field and the locomotor rating scale was determined after a 3 minute observation session. Recovery of hindlimb movements was assessed 1 day after injury, 7 days after injury, and once a week for a duration of 8 weeks.

For Catwalk gait analysis, animals were first trained to walk on the Catwalk runway in an uninterrupted manner. On the test day, four runs per animal were obtained as valid runs. Individual footprints were determined manually using Catwalk software. Then, the software automatically calculated five gait parameters. The angle of hindpaw rotation was defined as the angle (in degrees (°)) of the hindpaw axis relative to the runway axis. An increase in rotation angle indicates external rotation of the hindpaws. The base of support was measured as the width of the area between the left and right hindpaws. Values from both hindpaws were averaged to calculate the stride length and paw angle values. The footprints of the hindpaws tend to overlap with those of the forepaws during walking in uninjured animals. However, injured animals often lose this coordination between the hind- and forepaws. Therefore, the relative position of the fore- and hindpaws was obtained by directly measuring the distance between the center pads of ipsilateral fore- and hindpaws in each step cycle. Regularity index was used for an objective analysis of gait coordination and calculated from the number of normal step sequence patterns multiplied by four and divided by the total amount of paw placements.

Experimental Results 1

Synthesis and Characterization of I-5

Figure 2A:
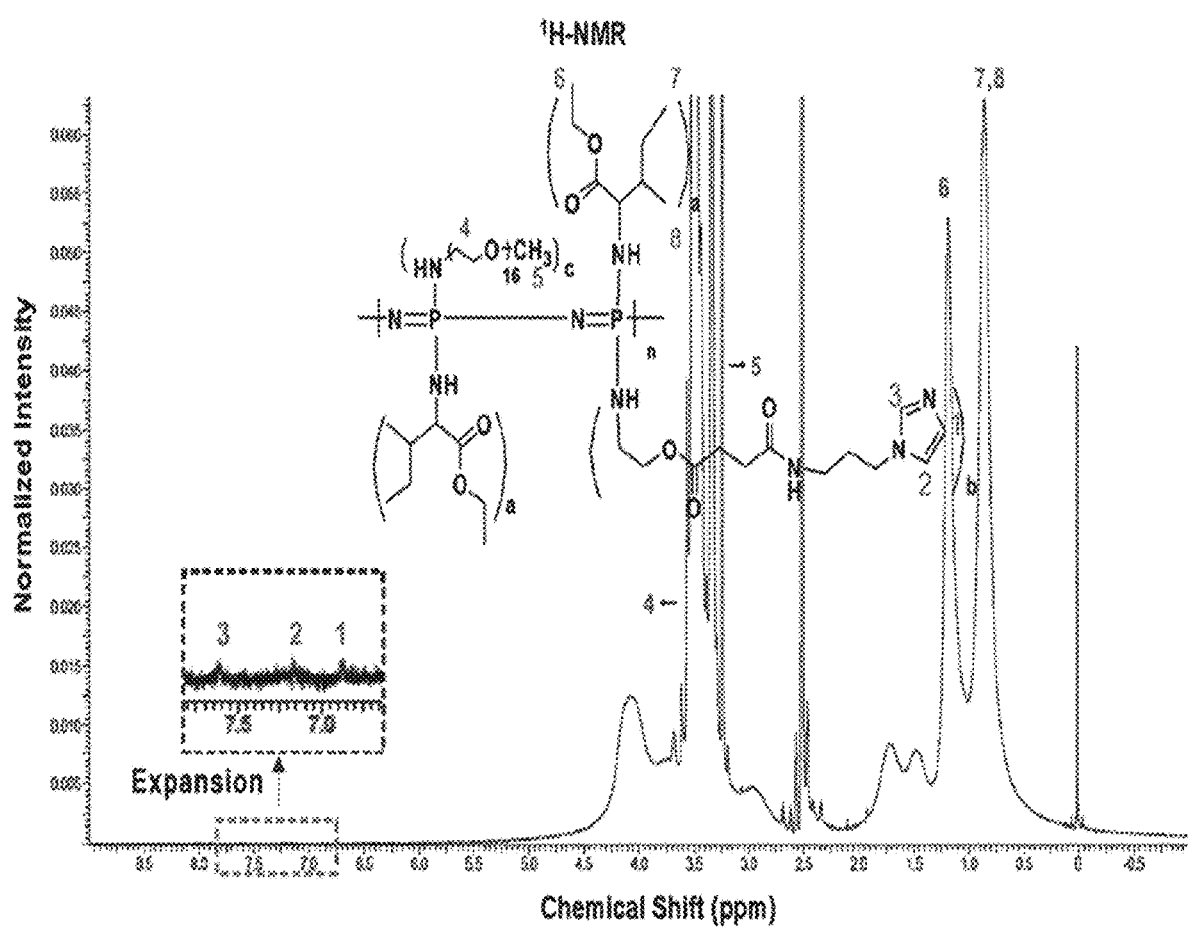
Figure 2B:
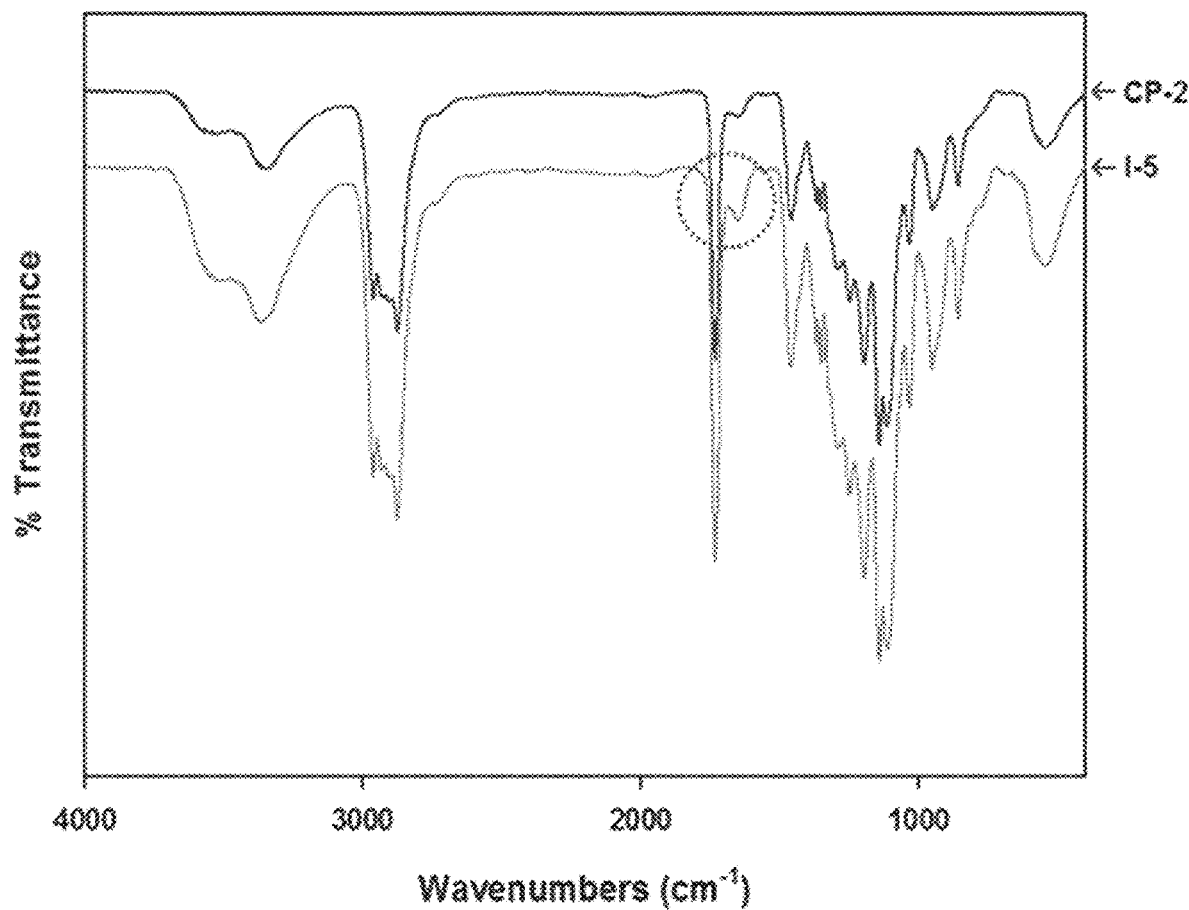

I-5 was synthesized through conjugation of imidazole to Polymer II (CP-2) by carbodiimide cross-linking between the amine group of 1-(3-aminopropyl)imidazole and the carboxyl group of Polymer II (FIG. 1). The existence of the imidazole group in I-5 was confirmed by the presence of imidazole peaks in the $^1$H-NMR spectrum and by an increase of the C=O peak, corresponding to the amide bond in Fourier Transform InfraRed (FT-IR) spectroscopy data (FIGS. 2A and 2B). The molecular weight of I-5 ranged from about 14 kDa to 18 kDa.

Figure 3A:
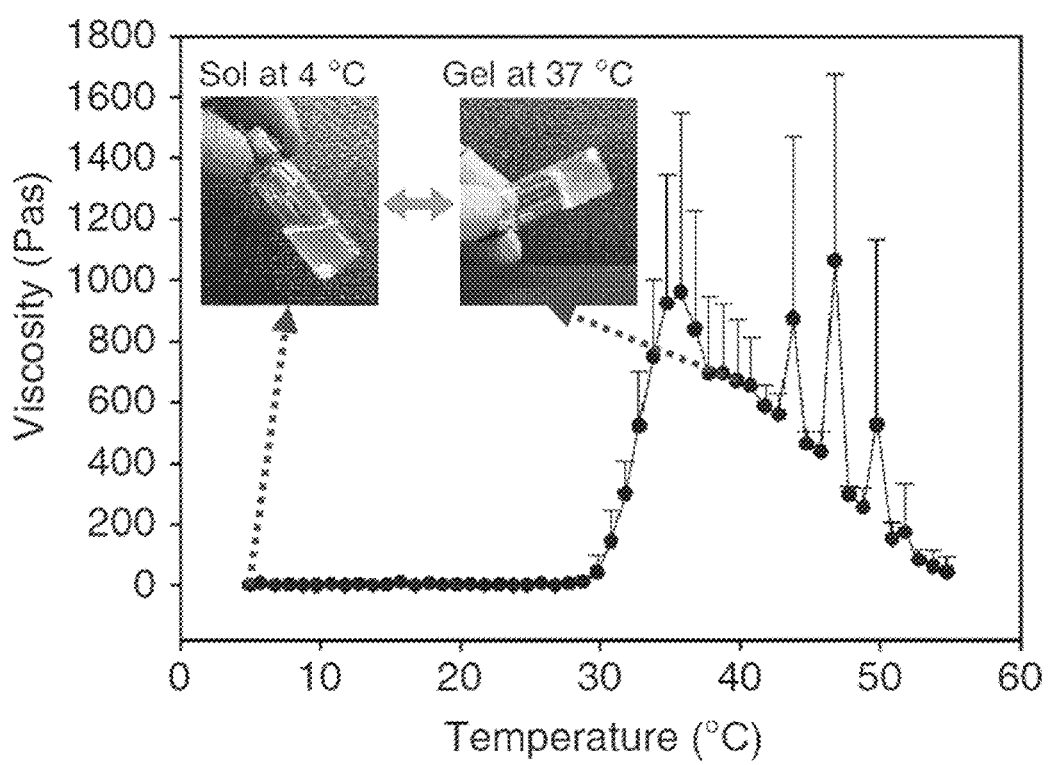

Additionally, the results of viscosity measurement of I-5 hydrogel are as follows. As shown in FIG. 3A, the viscosity rose abruptly when the temperature reached 30° C., causing a phase transition from sol to gel state. The viscosity at body temperature was about 600 Pa·s, which indicates that the material injected in vivo has physical strength sufficient to support and maintain the shape of the hydrogel.

Figure 3B:
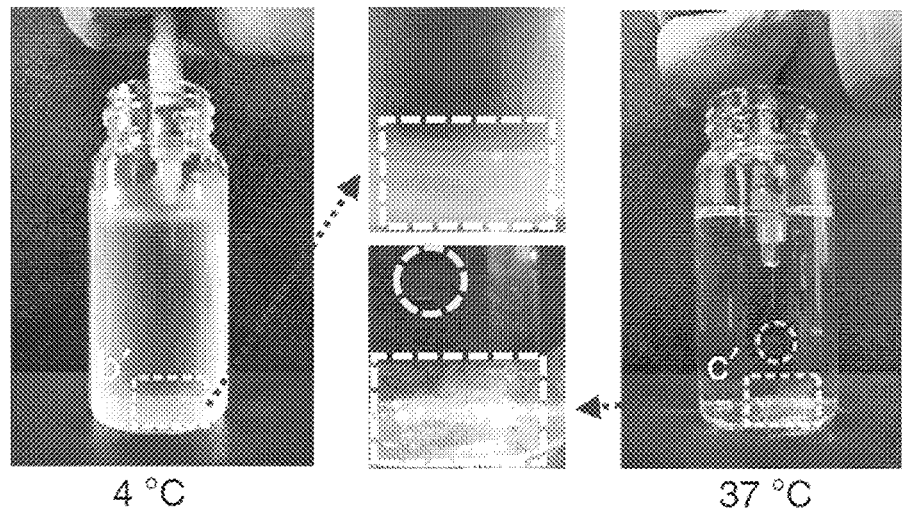
Figure 3C:
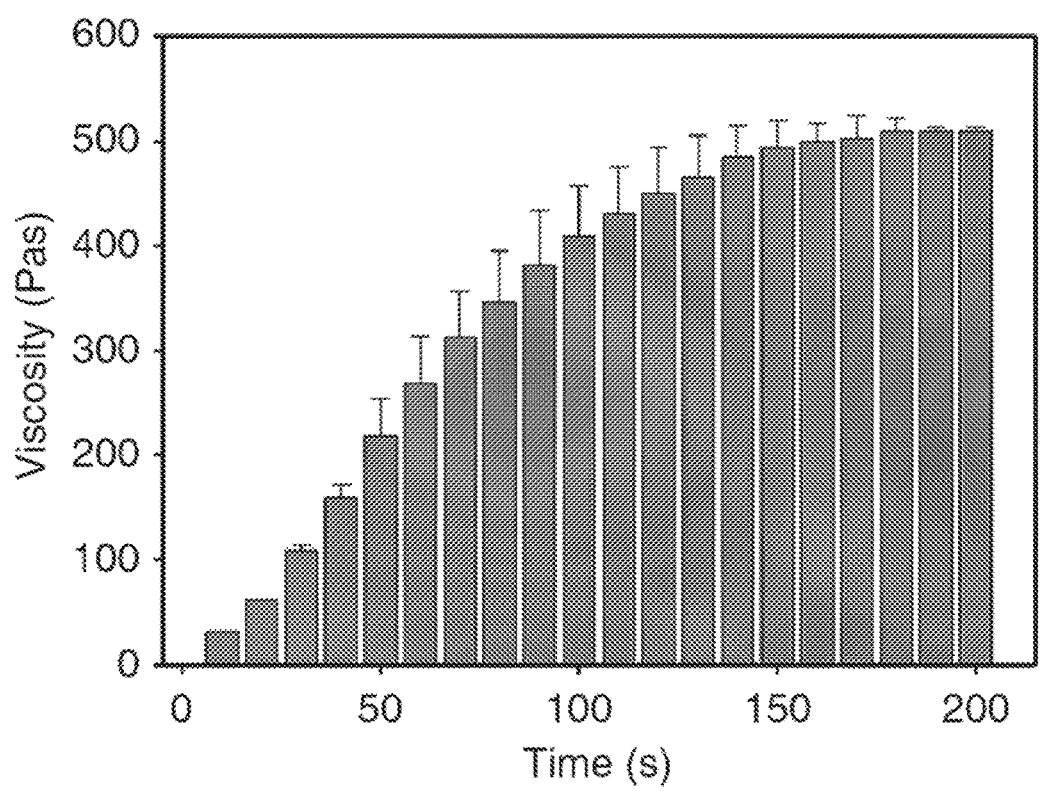

Additionally, the rapidity of the gelation process was visualized by injecting a polymer solution into distilled water either at 4° C. or 37° C. As shown in FIG. 3B, immediately after injection of the polymer solution into the water at 37° C., rod-like gel formation was observed (dotted circle marked as c' in the right figure of FIG. 3B). Several seconds later, opaque gel-like materials accumulated at the bottom of the glass vial (dotted rectangle marked as c' in the right figure of FIG. 3B). In contrast, when the polymer solution was injected into the water at 4° C., there was no evidence of gelation (dotted rectangle marked as b' in the left figure of FIG. 3B). The temporal changes in viscosity were measured in the case set at 37° C., and the results are shown in FIG. 3C. As a result, within 10 seconds of temperature being set at 37° C., the viscosity of the hydrogel solution began to form a gel-type material with a viscosity of about 50 Pas. Then, the viscosity rose very rapidly thereafter and reached a stationary phase at 150 seconds. That is, it was confirmed that gelation was completed within a few minutes in the water at 37° C.

Figure 3D:
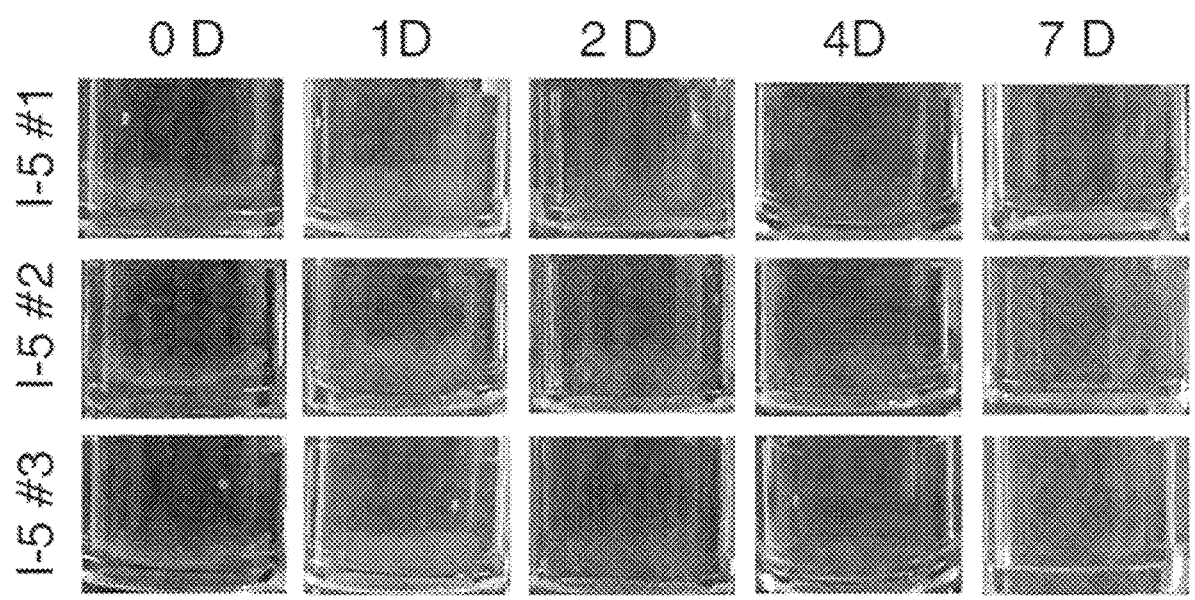

Additionally, in vitro stability test was performed to obtain information on degradation behavior. As shown in FIG. 3D, in the solution set at 37° C., I-5 hydrogel seemed to be swollen at 1 or 2 days in vitro, and then began to dissolve by 4 days. By 7 days, the gel mass disappeared and I-5 seemed to be completely dissolved. These results suggest that I-5 hydrogel was decomposed within 7 days in vitro, and that there is a high likelihood that the decomposition may proceed more rapidly in vivo.

Figure 4A:
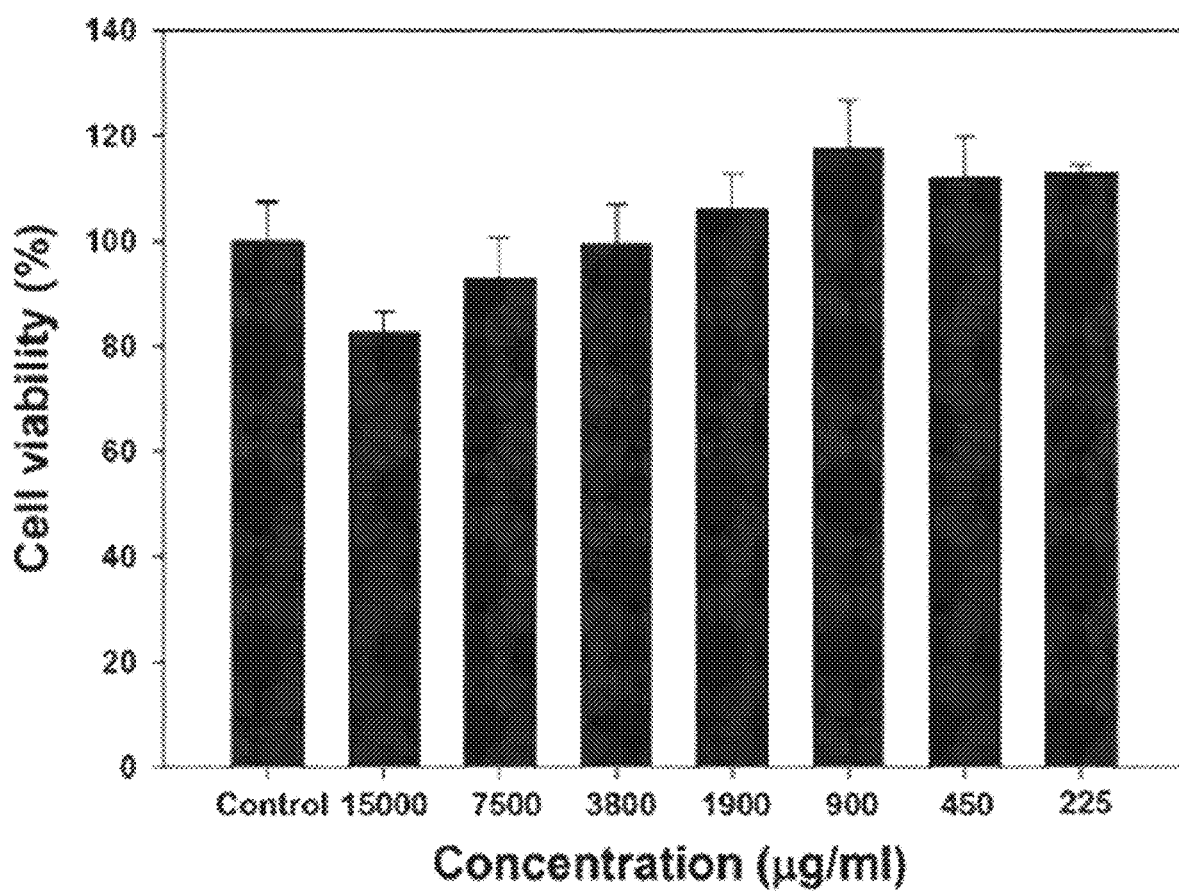
Figure 4B:
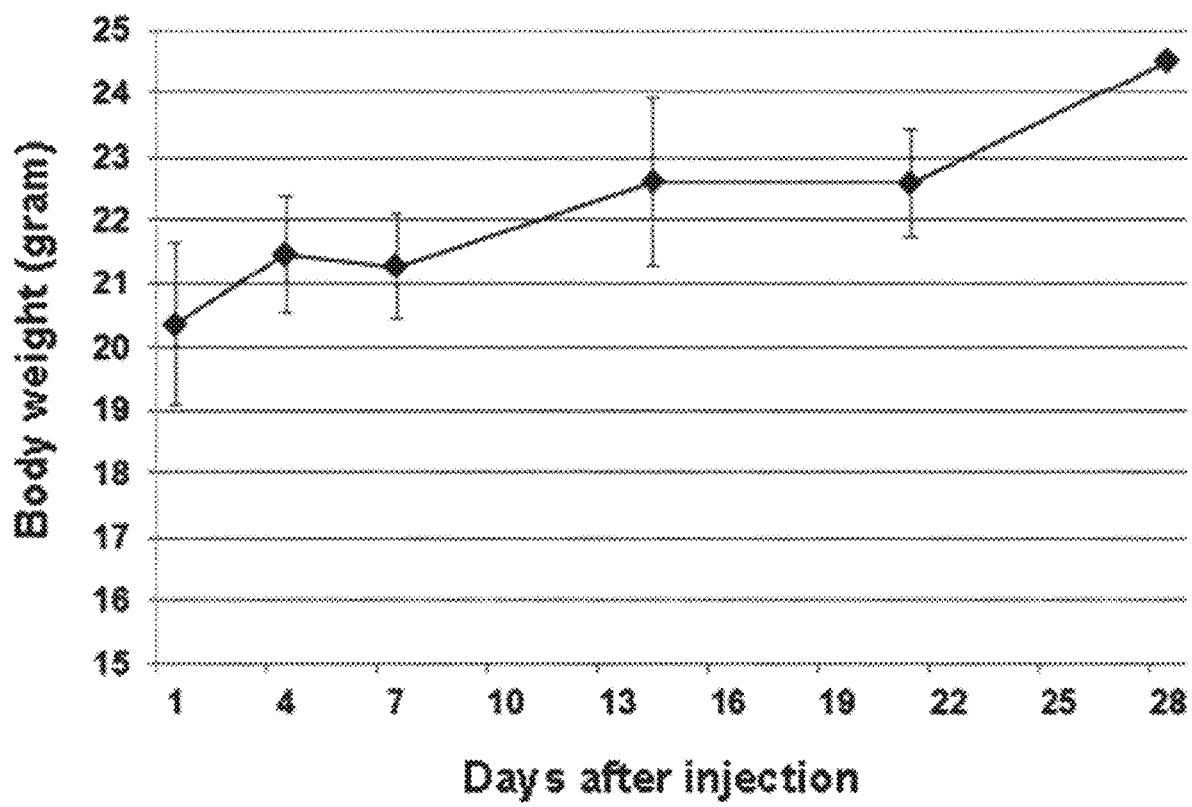
Figure 4C:
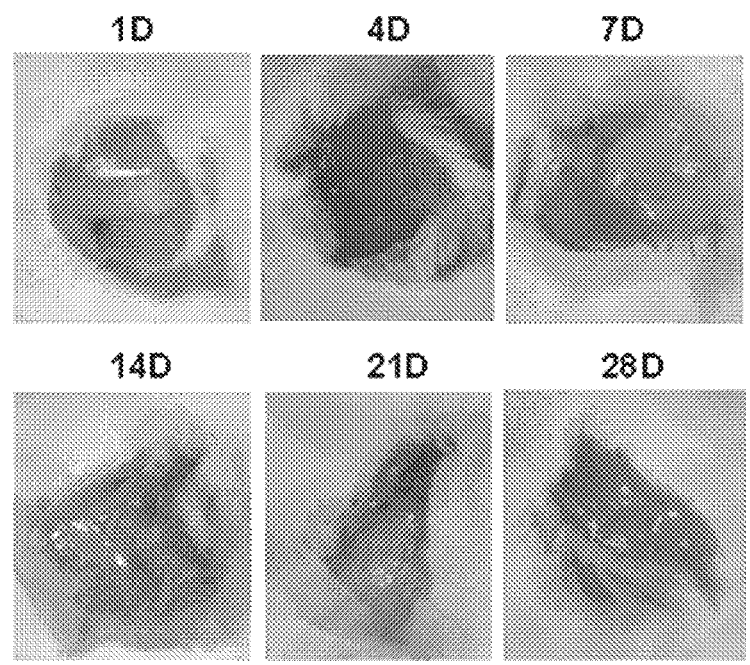

As shown in FIG. 4A, it was confirmed that the viability of cultured cells was not significantly affected by the I-5 polymer solution at various concentrations. Additionally, the mean body weight increased as expected (FIG. 4B), suggesting that the I-5 injection did not invoke systemic inflammatory reactions. Additionally, the inspection of local injection sites also revealed no sign of inflammation or necrosis in the subcutaneous tissue surrounding the hydrogel (FIG. 4C).

From these results, it was confirmed that the I-5 polymer hydrogel is non-cytotoxic in vitro and also does not elicit foreign body reactions in vivo.

Experimental Results 2

Effect of I-5 on Treatment of Cystic Cavities after Spinal Cord Injury

Figure 5A:
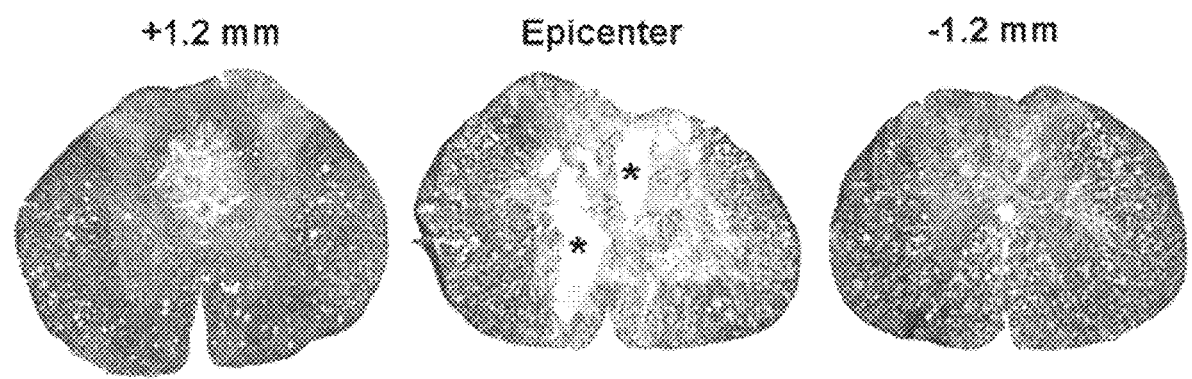
Figure 5B:
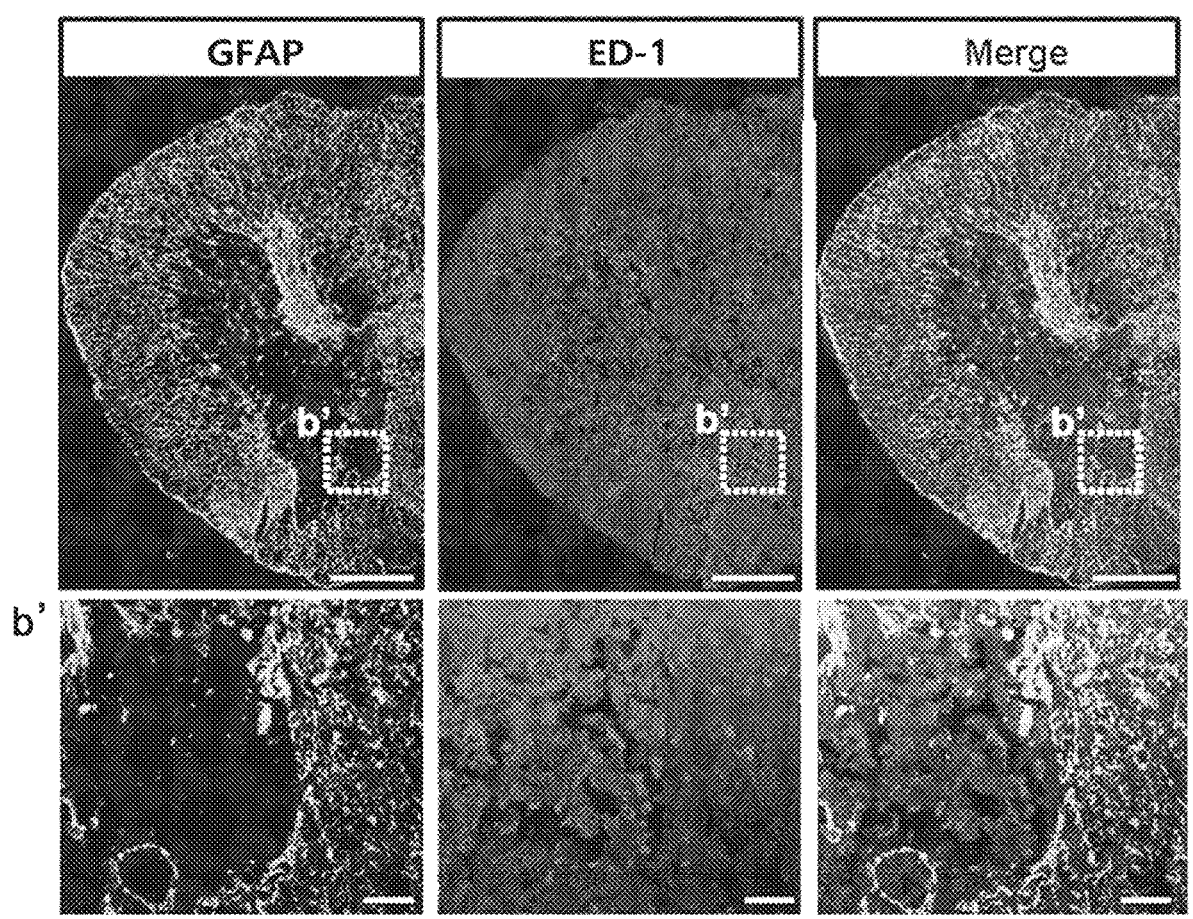

A previous study showed that cystic cavities began to form as early as 1 week after contusion injury and progressively enlarged up to the 4-week time point, and no further expansion of the cystic cavities was observed after the 5-week time point after injury (4 weeks after injection) (Ek, C. J. et al. Spatio-temporal progression of grey and white matter damage following contusion injury in rat spinal cord. *PLoS ONE* 5, e12021 (2010)). In fact, at 1 week after injury, the present inventors observed that rather large cystic cavities were already formed at the epicenter (asterisks in FIG. 5A). At this time point, a transverse spinal cord section was observed by staining with GFAP and CD68 antibodies, and the non-cystic lesions were shown to be filled with ED-1 positive macrophages which were surrounded by glial fibrillary acidic protein (GFAP) positive astrocytes (FIG. 5B).

Figure 6A:
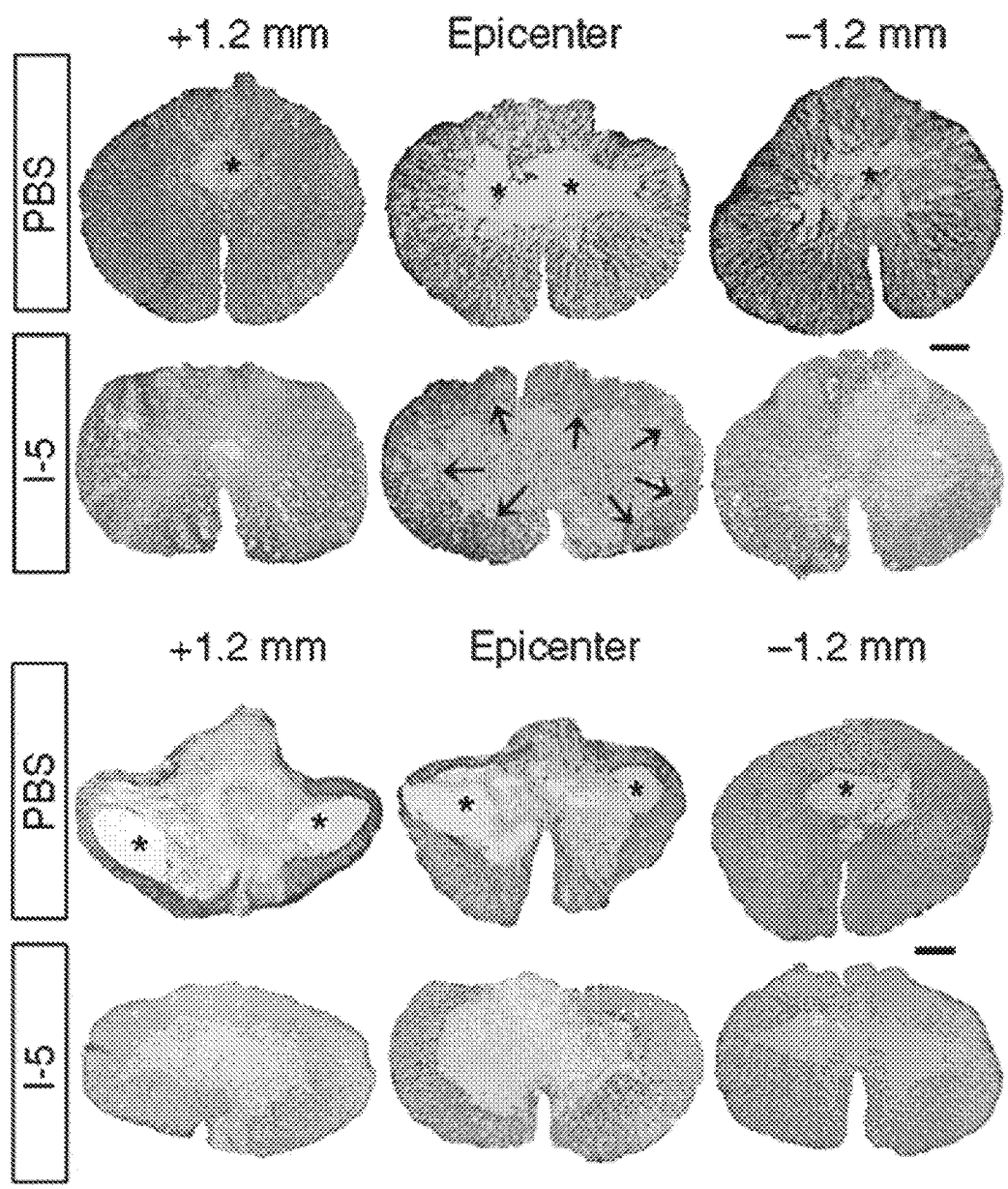
Figure 6B:
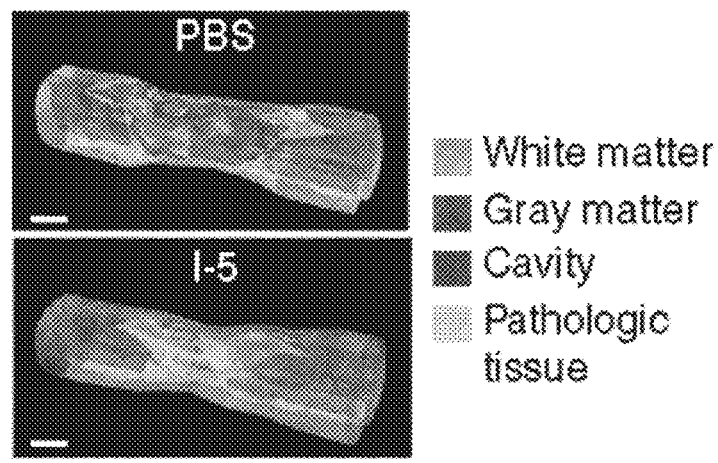
Figure 6C:
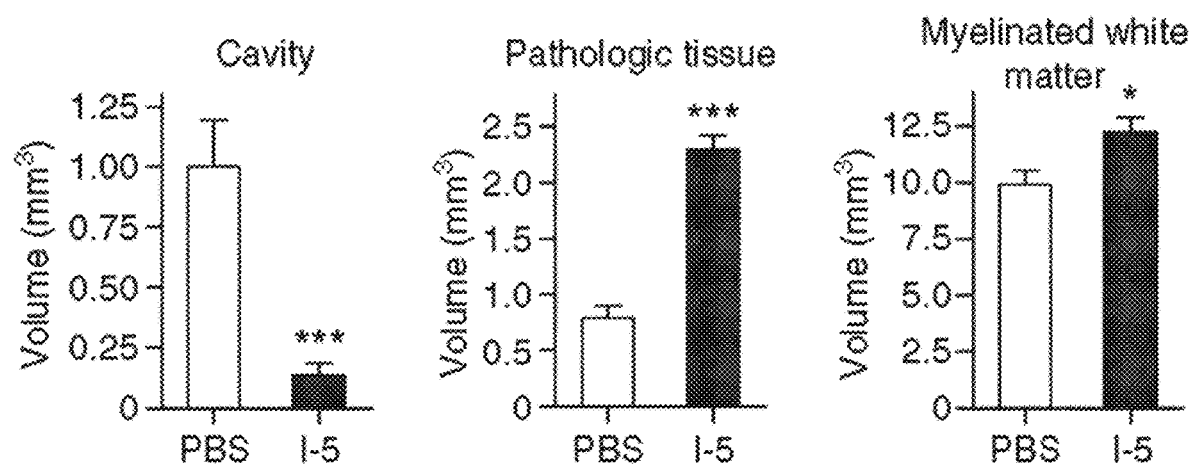

Based on the results of the previous study, the presence of cystic cavities at the 4-week time point after injection was observed. As a result, it was revealed that cystic cavities became larger extending rostrocaudally more than 2.0 mm away from the epicenter in animals injected with the control PBS (FIG. 6A). In contrast, the I-5 injection resulted in almost complete disappearance of cystic cavities in all of the animals that received I-5 injection (FIG. 6A). The epicenter region was filled with eosin-stained ECM-like tissue instead of cystic cavities (FIG. 6A, I-5, top). GFAP immunostaining showed that the ECM-like tissue was largely devoid of astrocytes, but surrounded by astrocytic scars (FIG. 6A, I-5, bottom). As illustrated in FIG. 6C, the mean volume of cystic cavities was significantly reduced in animals treated with I-5 injection (1.00 mm$^3$ vs. 0.14 mm$^3$; $t_{(14)}$=4.292, p<0.001). The volume of pathologic tissue, which was defined as the area without normal tissue architecture, was significantly increased in animals treated with I-5 (FIG. 6C), probably due to the eosin-stained ECM-like tissue filling cystic spaces. The I-5 injection significantly increased the volume of myelinated white matter (FIG. 6C). There were no detectable remnants of gel-like materials within the spinal cord tissue.

Figure 6D:
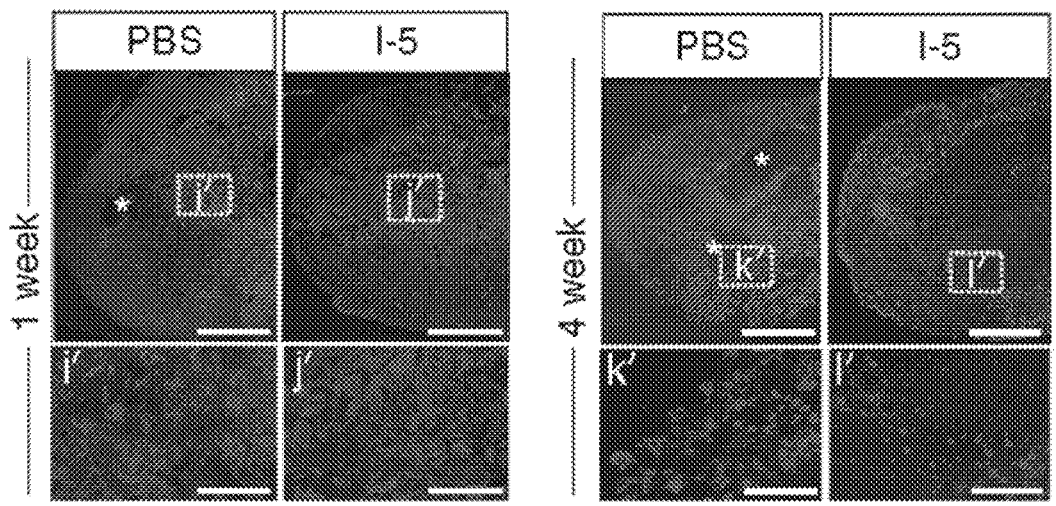
Figure 6E:
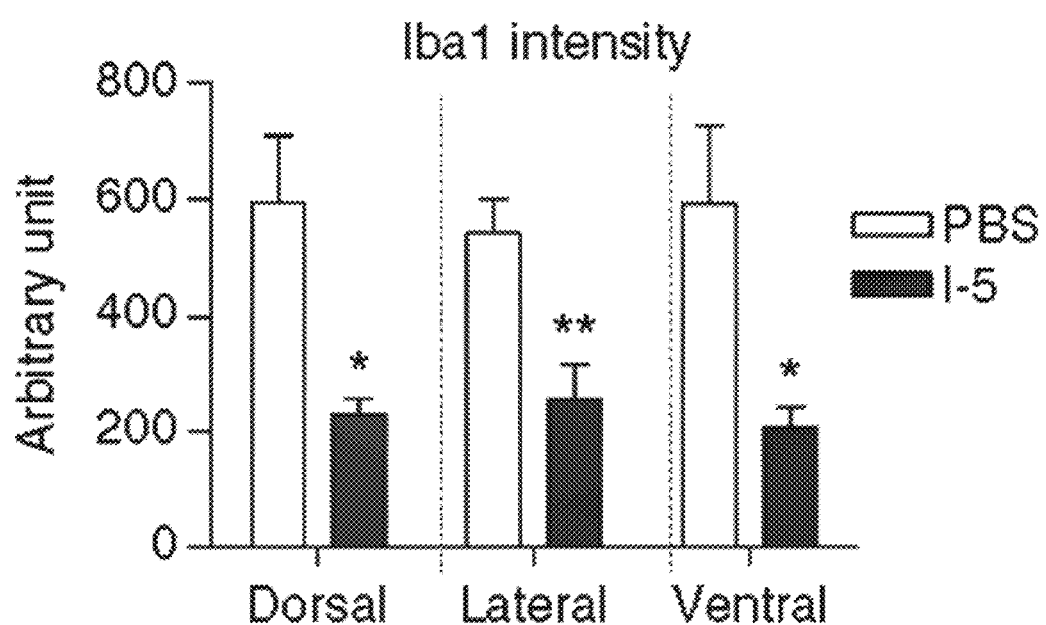

To examine the possibility that I-5 may provoke exaggerated inflammatory reactions in the spinal cord tissue, the present inventors have examined the intensity of immunoreactivity for Iba1, a marker of inflammatory macrophages. At 1 week after injection, intense Iba1 immunoreactivities occurred at the lesion cores in animals treated with PBS or I-5 injection to a similar extent (FIG. 6D). At 4 weeks after injection, strong Iba1 immunoreactivities remained surrounding cystic cavities in animals treated with PBS injection (FIGS. 6D and 6E). In contrast, the intensity of Iba1 immunoreactivity was significantly attenuated at the border surrounding the ECM-like tissue filling the central region (FIGS. 6D and 6E). This data suggests that I-5 did not provoke excessive inflammatory reactions and that bridging cystic cavities with I-5 may actually suppress post-injury inflammatory processes.

Experimental Results 3

I-5 Induces Formation of Fibronectin-Rich Fibrotic ECM

Figure 7:
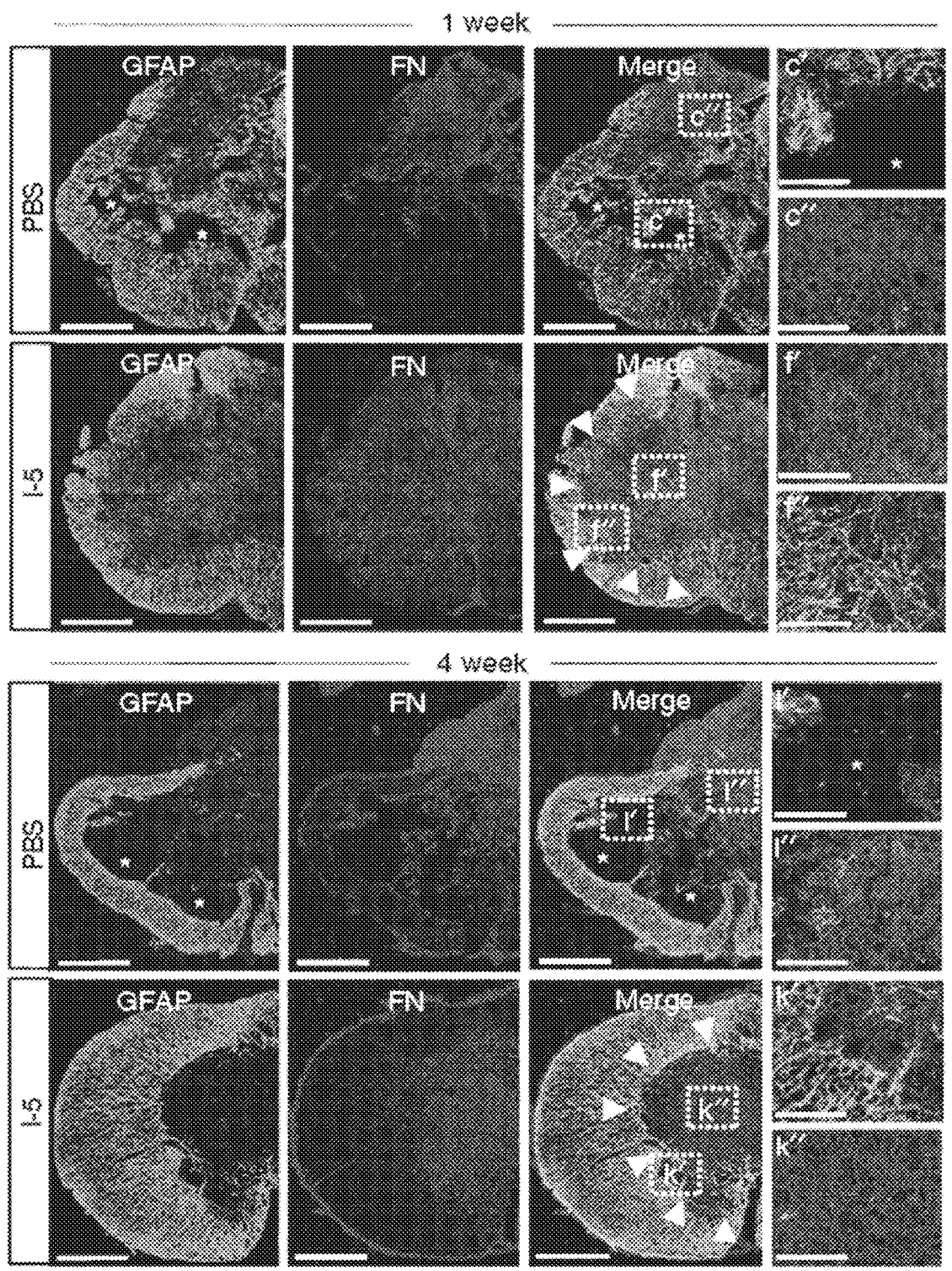
FIG. 7 shows the results of ECM remodeling by I-5 hydrogel injection, in which portions indicated as c', c'', f', and f'' show the images of transverse spinal cord sections of rats obtained 1 week after injection of PBS or I-5 hydrogel; and portions indicated as i', i'', k', and k'' show the images of transverse spinal cord sections of rats obtained 4 weeks after injection of PBS or I-5 hydrogel.

Next, the present inventors have characterized the ECM-like tissue at the epicenter region where cystic cavities are expected to be present without I-5 injection. In animals injected with PBS, GFAP-positive astroglia increased not only in the white matter but also in the central region of the injured tissue 1 week after injury (FIG. 7a, GFAP, top). There were also areas devoid of GFAP immunoreactivity (FIG. 7a, top). In contrast, animals injected with I-5 showed more widespread formation of fibronectin-positive matrix, whereas GFAP immunoreactivity was confined within the spared white matter (FIG. 7, 2$^{nd}$ panel). As a result, the fibronectin-positive areas were largely separated from the GFAP-positive white matter, although the two areas were not completely segregated (FIG. 7, 2n$^d$ panel).

At 4 weeks after injury, cystic cavities were enlarged compared to the 1 week time point in animals injected with PBS (FIG. 7, 3$^{rd}$ panel). The expansion of cavity spaces was accompanied by shrinkage of the fibronectin-positive matrix (FIG. 7, 3$^{rd}$ panel). In contrast, the fibrotic matrix in animals injected with I-5 seemed to be consolidated at the central region. There was an increase in the density as well as intensity of fibronectin immunoreactivity (FIG. 7, bottom). The segregation between the fibronectin- and GFAP-immunoreactive areas became more obvious than at the 1 week time point, establishing a discrete border between the two cellular compartments.

Figure 8A:
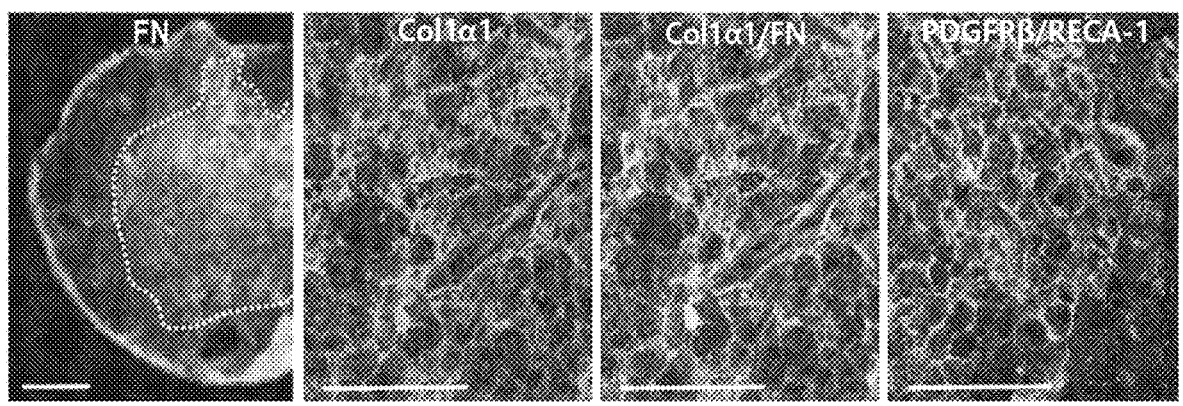
Figure 8B:
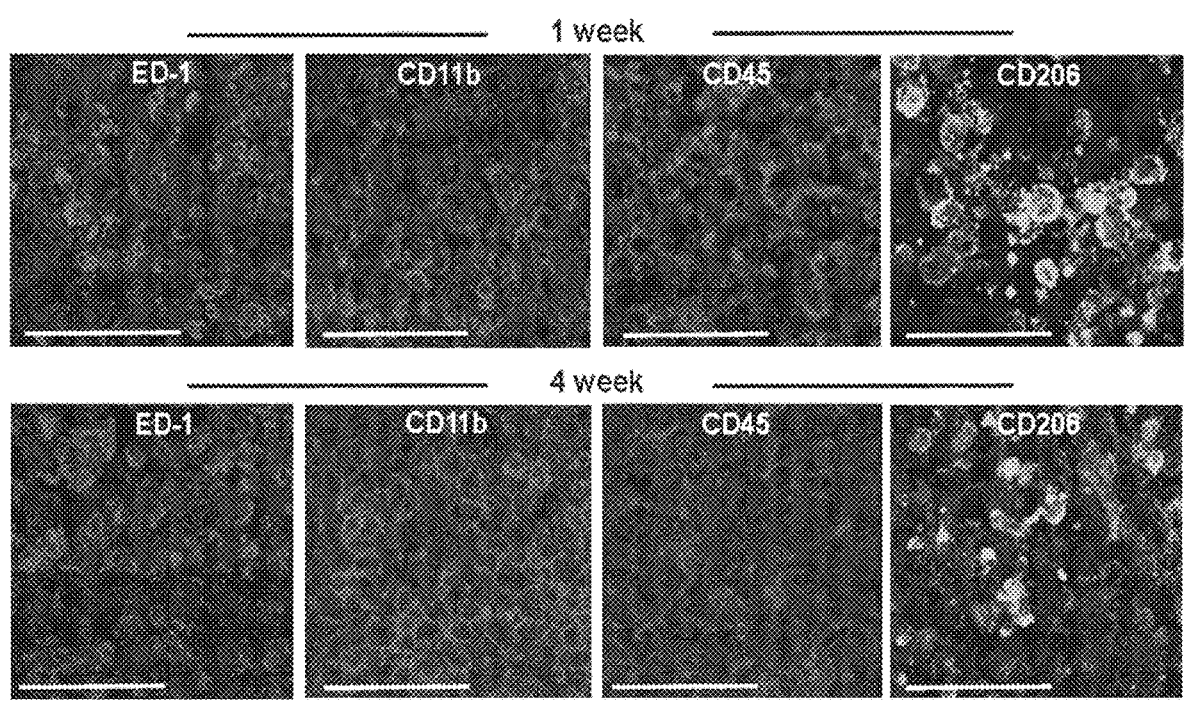

In the previous study, the present inventors had discovered that the fibronectin-rich fibrotic matrix formed by I-5 injection bore resemblance to the fibrotic scar observed after contusive spinal cord injury (SCI) in rats, where cystic cavities did not develop. Collagen 1α1-expressing perivascular fibroblasts are the major cellular source of fibrotic scars in rats. Immunofluorescence staining against fibronectin and collagen 1α1 showed co-localization within the fibronectin-rich ECM formed by I-5 injection (FIG. 8a). Cells that are positive for PDGFR-beta, a marker for perivascular fibroblasts, were frequently found within the matrix encircling RECA-1 immunoreactive endothelial cells (FIG. 8a, 4$^{th}$ box). It was reported that macrophages mediate the assembly of fibronectin matrix in fibrotic scars in mice. The present inventors have confirmed that the fibronectin-rich ECM was densely populated by ED1- and CD11b-positive macrophages at 1 and 4 weeks after I-5 injection (FIG. 8b). These macrophages were highly likely of a hematogenous origin because CD45 immunoreactivity was also observed at the 1 week time point (FIG. 8b, top). The intensity of CD45 immunoreactivity tended to decline but still clearly persisted at the 4 week time point (FIG. 8b, bottom). Those macrophages were also positive with CD206, which is a maker of M2 polarization (FIG. 8b).

These results suggest that fibroblasts and fibrotic scar formation may play a critical role in the I-5-induced elimination of cystic cavities. A previous study demonstrated that administration of the microtubule stabilizer Taxol can decrease fibrotic scar formation. To examine a potential causative role of fibrotic scarring in the bridging effects, I-5 hydrogel mixed with Taxol or PBS was injected. When I-5 was injected with Taxol (1 μg/μL), equal volumes of the agent and a 20 wt % solution of I-5 were mixed, yielding a final gel concentration of 10 wt %.

Figure 9A:
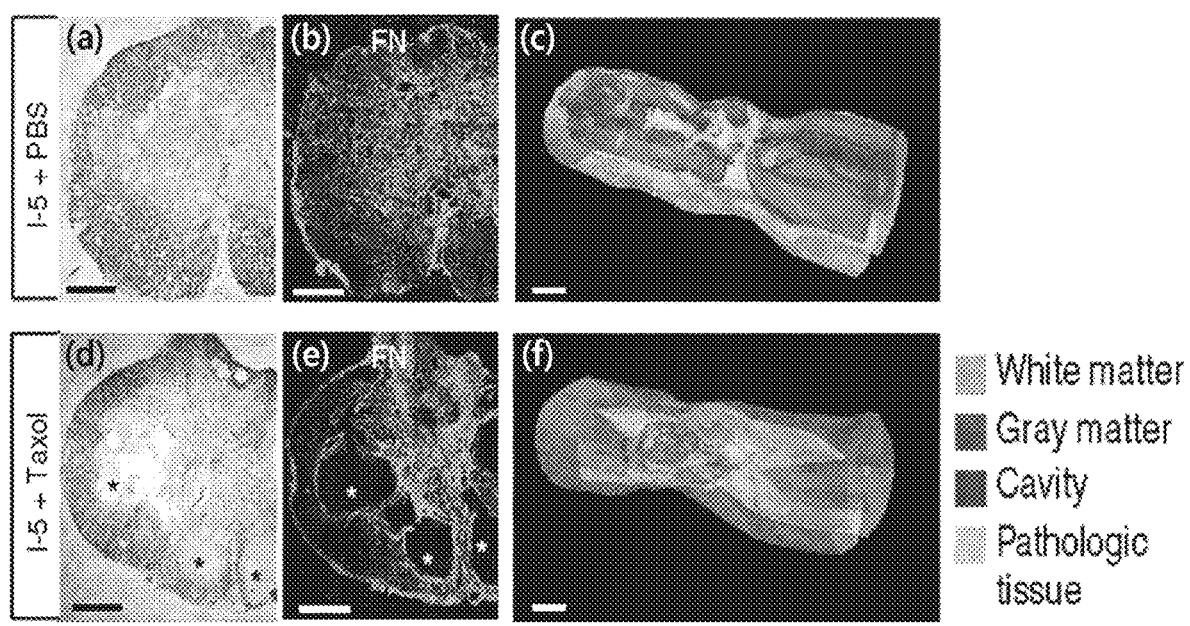
FIGS. 9A to 9B show the results of expansion of cystic cavities by taxol, in which FIG. 9A (top) shows the images of transverse spinal cord sections of rats, in which the I-5 hydrogel mixed with PBS or taxol was administered, stained with eriochrome cyanine and eosin.
Figure 9B:
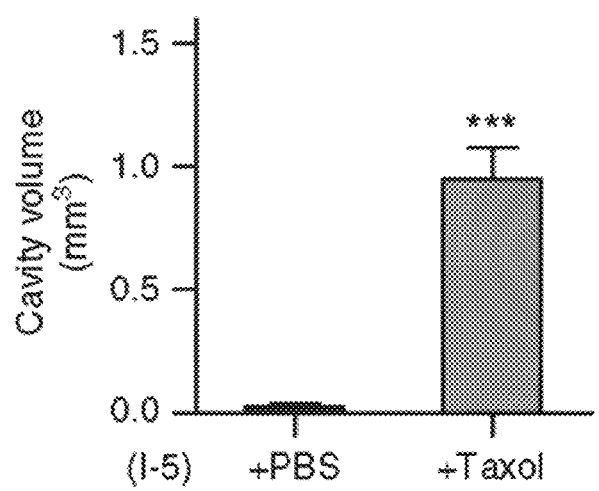

As expected, I-5 mixed with PBS prevented development of cystic cavities by inducing fibronectin-rich ECM formation (portions indicated as (a), (b), and (c) in FIG. 9A). The injection of I-5 in combination with Taxol resulted in a reduction of fibronectin-positive ECM and marked expansion of cystic cavities (portions indicated as (d), (e), and (f) in FIG. 9B).

Experimental Results 4

MMP-9 in Macrophages Mediates ECM Remodeling

Figure 10A:
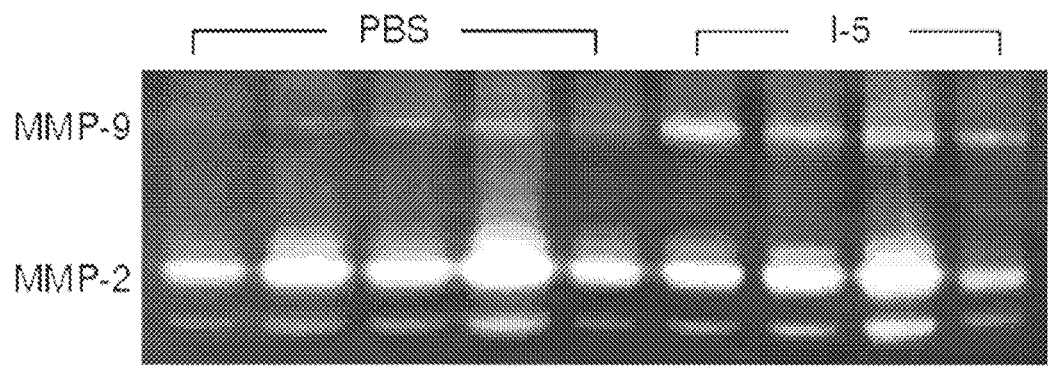
Figure 10B:
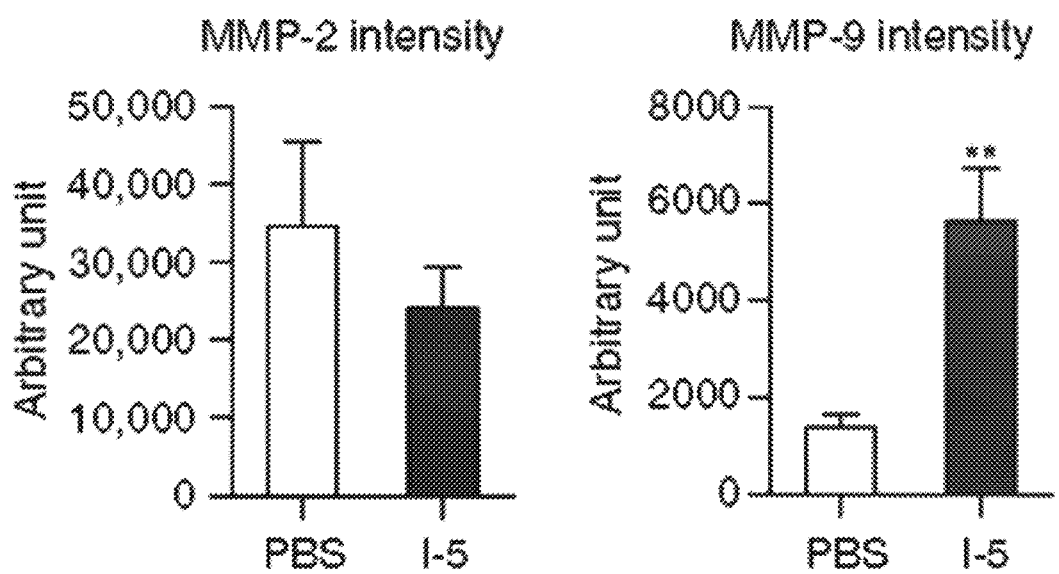
Figure 10C:
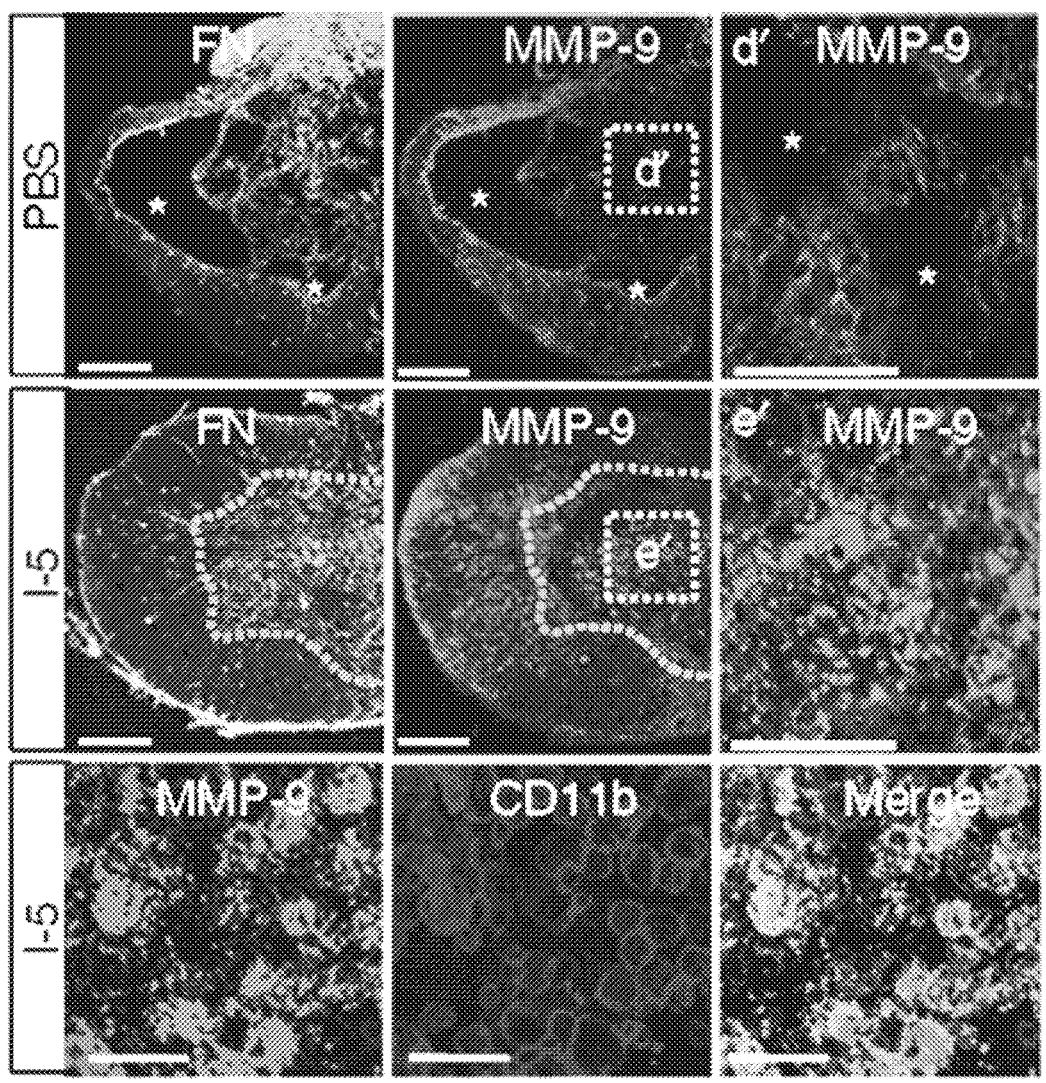

The present inventors have speculated that certain matrix remodeling enzymes may be involved in the formation of fibronectin-rich fibrotic matrix after I-5 injection. MMPs are zinc-dependent endopeptidases capable of modulating ECM proteins, and MMPs with gelatinase activity have beneficial roles in matrix remodeling and wound healing-associated fibrosis. In rats injected with hydrogel, the activity of MMP-9 was noticeably enhanced (FIGS. 10A and 10B). Meanwhile, the immunostaining to detect MMP-9 revealed very little immunoreactivity in the remaining matrix surrounding cystic cavities (FIG. 10C, top). In contrast, there was markedly increased expression of MMP-9 within the fibronectin-rich fibrotic matrix in animals injected with I-5 (FIG. 10C, middle). Additionally, the MMP-9 immunoreactivity appeared granular and was largely surrounded by immunoreactivity for the macrophage cell surface marker CD11b (FIG. 10C, bottom).

Figure 11A:
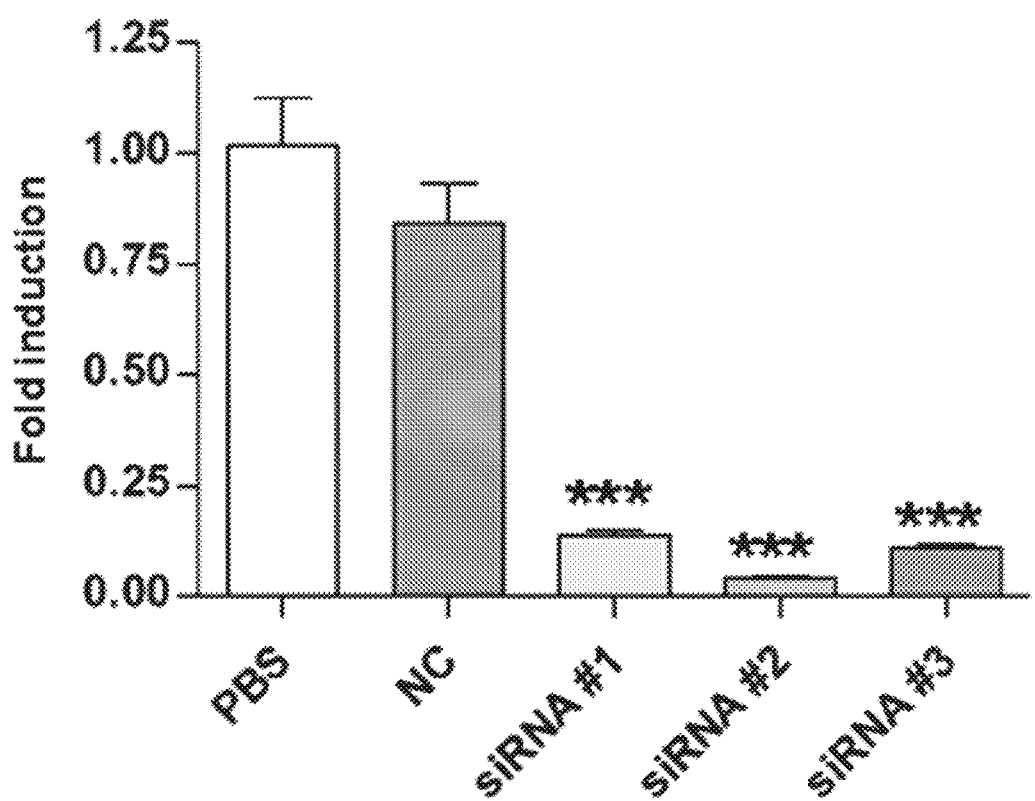
Figure 11B:
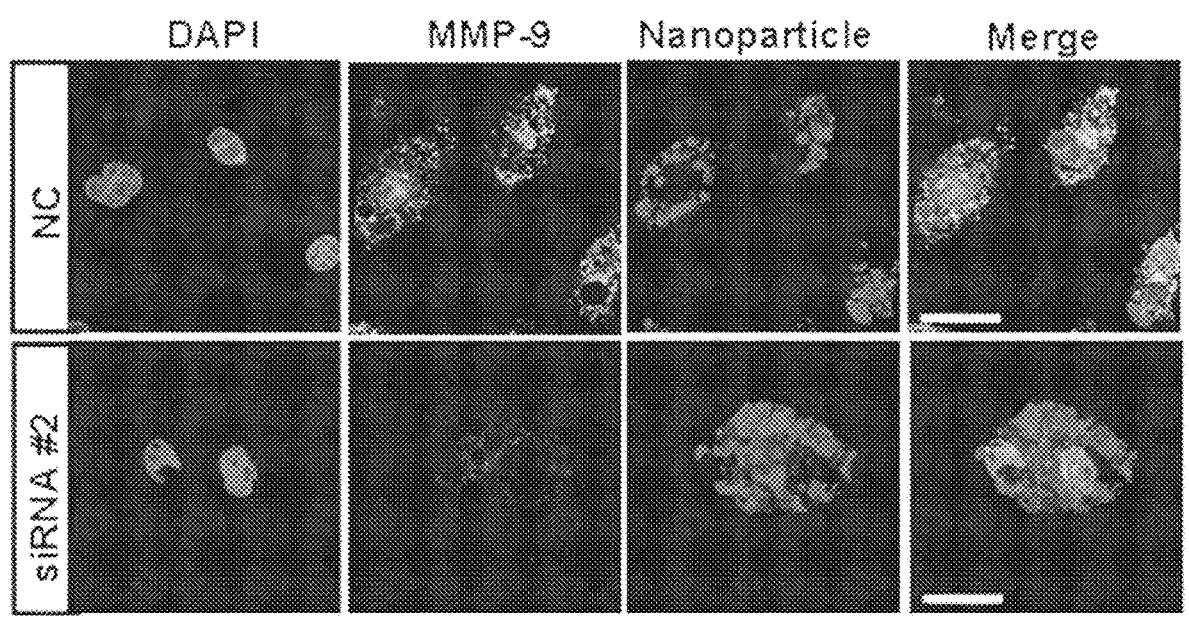
Figure 11C:
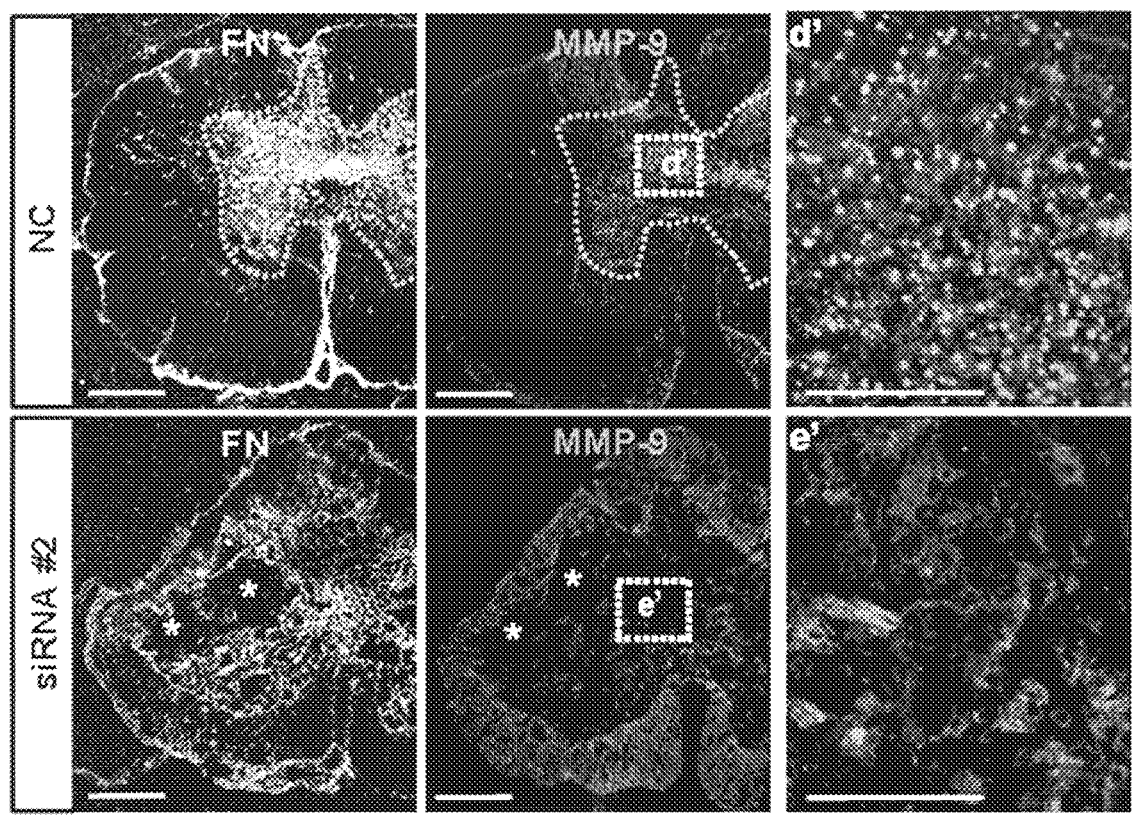

To determine whether MMP-9 mediates the fibrotic ECM remodeling induced by I-5 hydrogel, the present inventors have performed a knockdown experiment using MMP-9 siRNA delivered by nanoparticles. Suppression of MMP-9 expression by siRNA nanoparticles was validated in cultured peritoneal macrophages (FIGS. 11A and 11B). The injection of I-5 hydrogel mixed with MMP-9 siRNA nanoparticles, but not the injection of I-5 mixed with nanoparticles carrying non-targeting control siRNA, depleted MMP-9 immunoreactivity in the fibronectin-positive ECM (FIG. 11C).

Figure 10D:
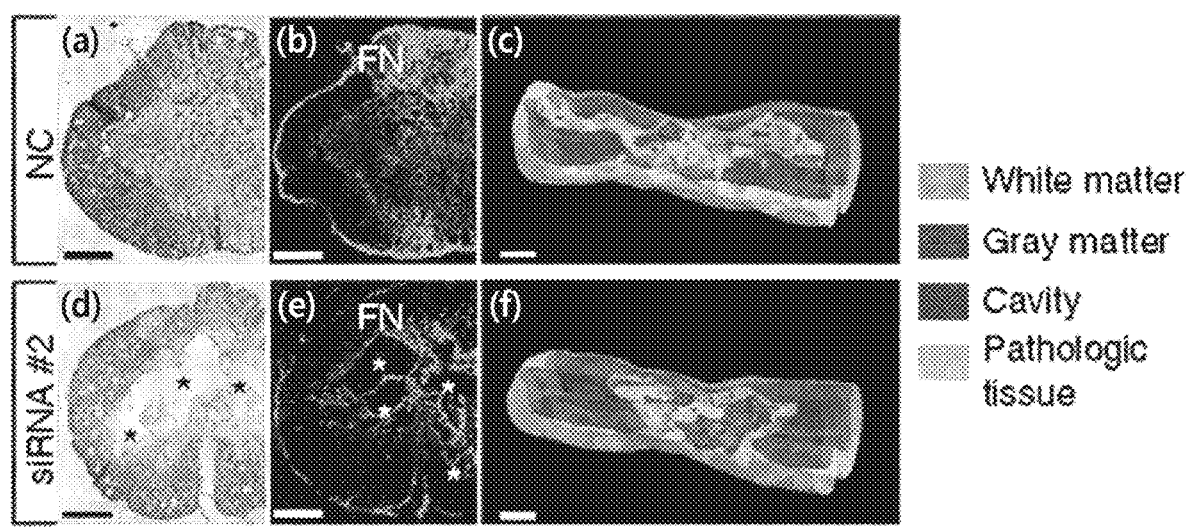
Figure 10E:
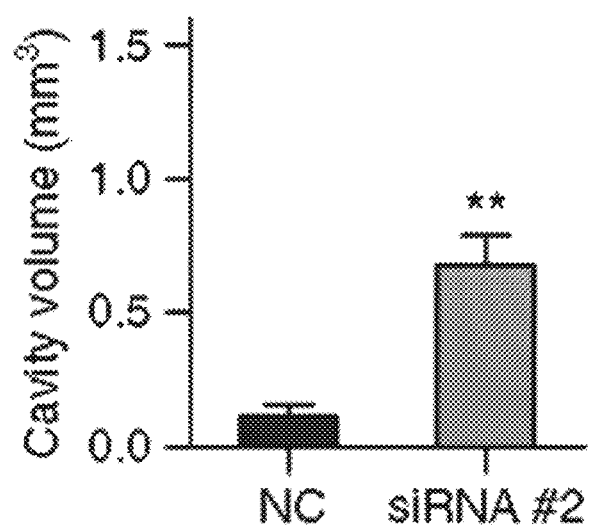

MMP-9 knockdown decreased formation of fibronectin-rich matrix at the lesion epicenter and substantially enlarged cystic cavities (FIGS. 10D and 10E). In contrast, the injection of I-5 with non-targeting siRNA almost completely eliminated cystic cavities (FIGS. 10D and 10E). These results indicate that macrophages within the fibronectin-rich matrix newly formed after I-5 hydrogel injection may produce MMP-9 enzymes that promote remodeling of fibrotic ECM at the epicenter.

Experimental Results 5

Interaction Between Macrophages and I-5 Hydrogel

The present inventors have tested whether I-5 hydrogel physically interacts with macrophages through binding to their histamine receptors. To visualize the interaction between the polymer hydrogel and macrophages in vitro, an I-5 solution was mixed with the hydrophobic fluorescent dye, Nile Red. It was expected that if the macrophages physically interact with the hydrogel, hydrophobic Nile Red dye in the nanoparticles would be delivered into the macrophages.

Figure 12A:
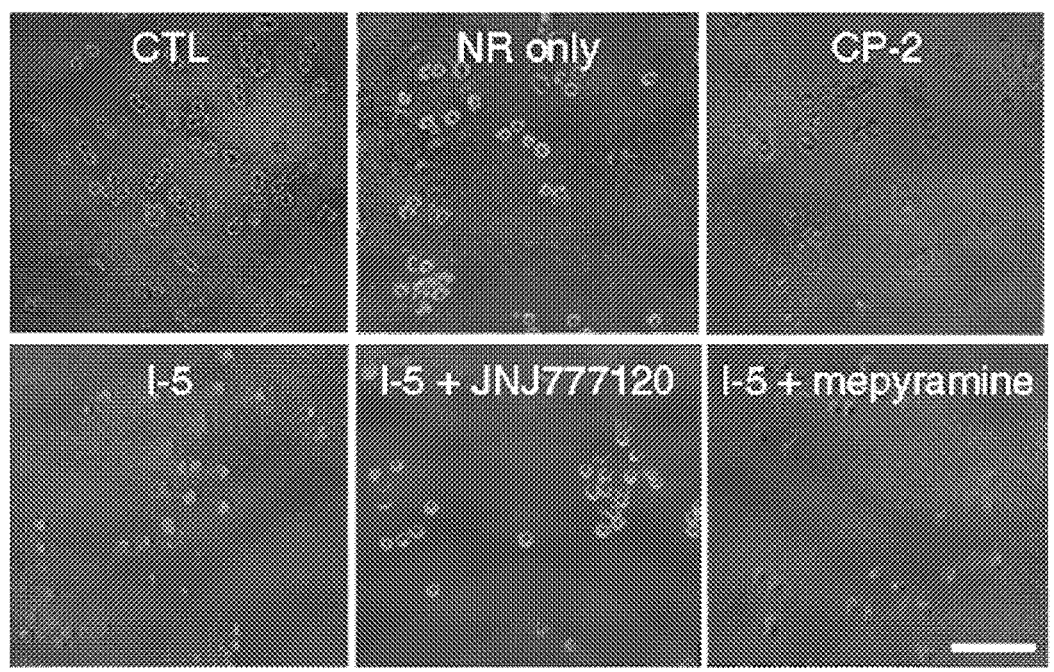
Figure 12B:
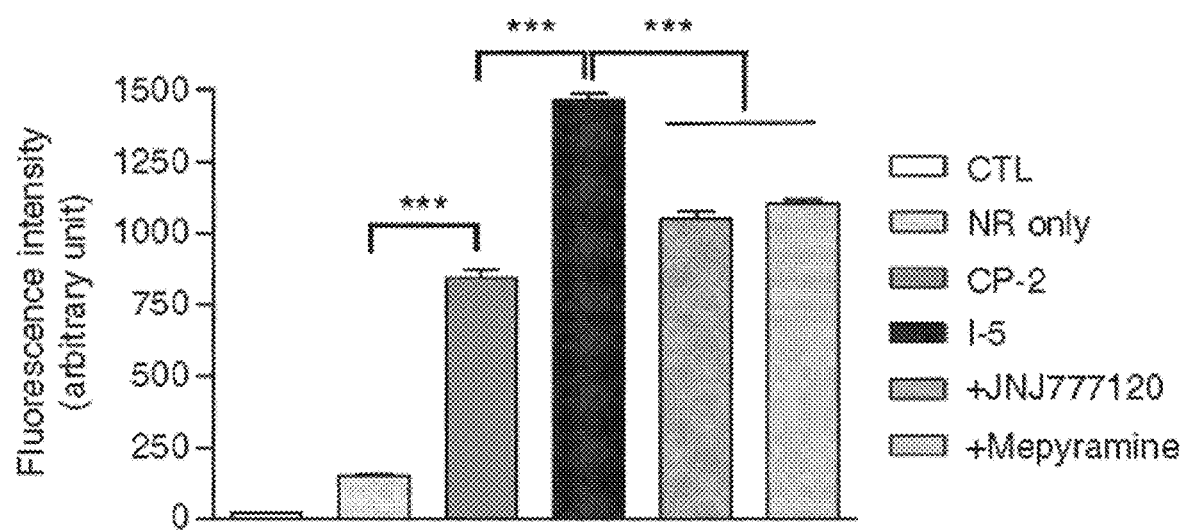

RAW 264.7 mouse macrophages cells were incubated with the nanoparticles which consisted of Nile Red and I-5 polymer micelles containing the imidazole group or CP-2 (carboxylic acid-terminated Polymer II in FIG. 1) without the imidazole group. When Nile Red dye alone was added to the culture medium, very little fluorescence was emitted from the macrophages (FIG. 12A). The macrophages exhibited discernible red fluorescence after incubation with the nanoparticles composed of CP-2. However, the fluorescence intensity was markedly higher when treated with the I-5 nanoparticles (FIGS. 12A and 12B), demonstrating that the presence of the imidazole group enhances the interaction between the hydrogel and macrophages. The red fluorescence in macrophages was lower after pretreatment with JNJ777120 or mepyramine, H4R, and H1R inhibitors, respectively (FIGS. 12A and 12B), suggesting that the imidazole group and histamine receptors in the macrophages mediate the interaction between the polymer and macrophages.

Figure 12C:
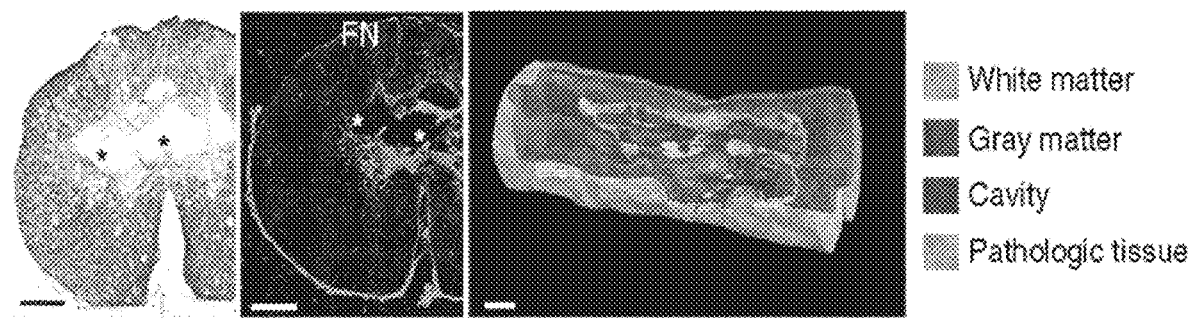
Figure 12D:
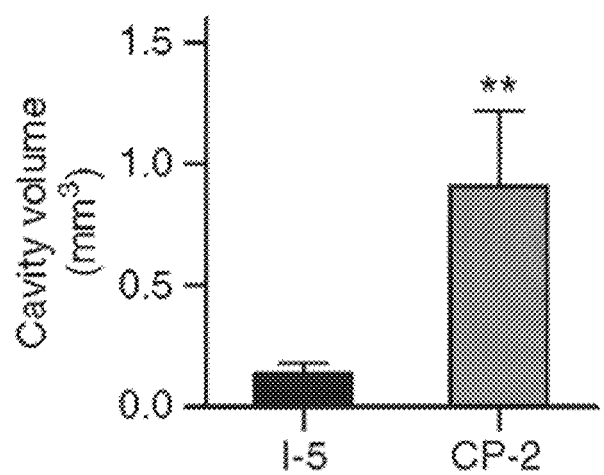
Figure 13A:
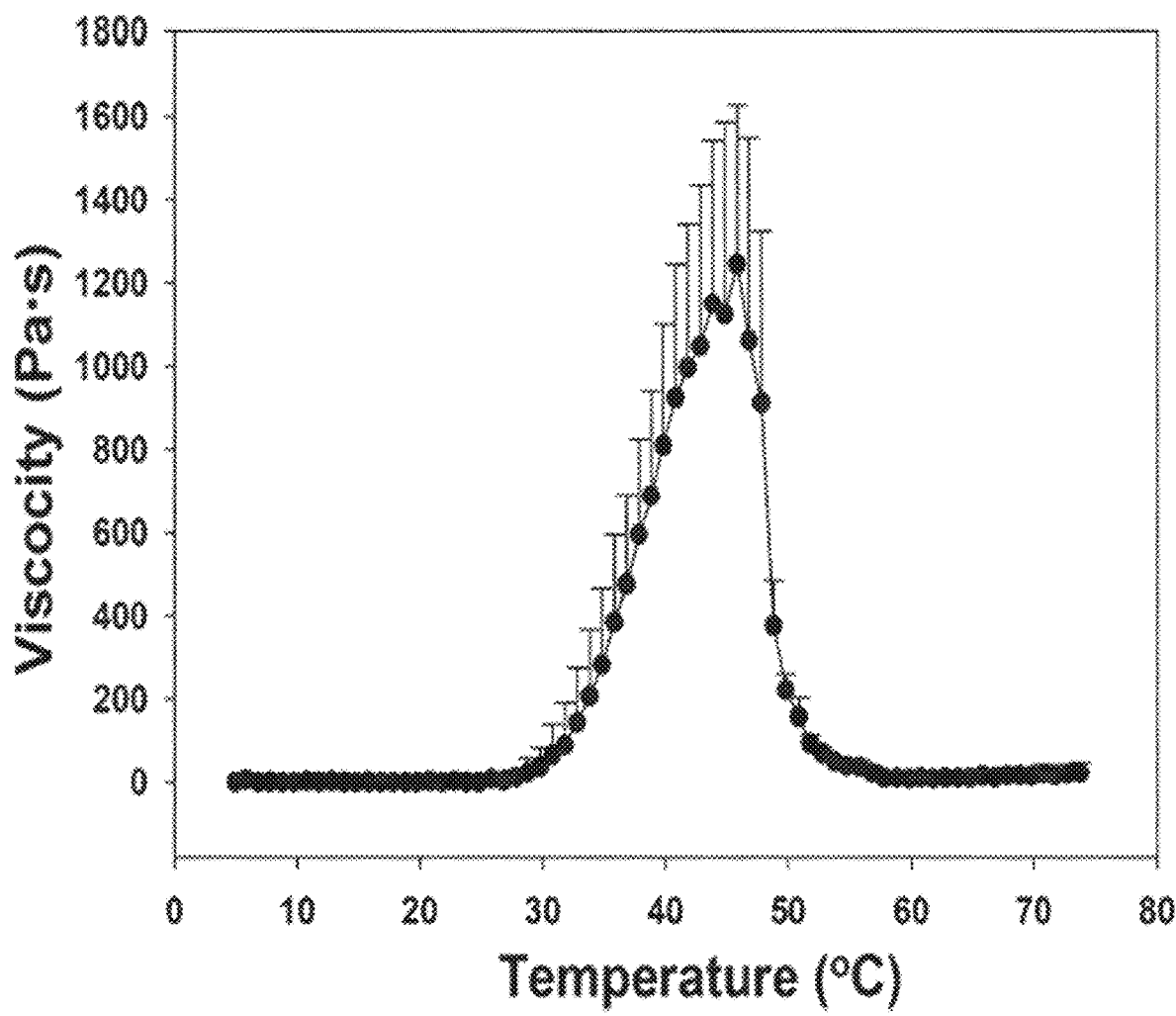
Figure 13B:
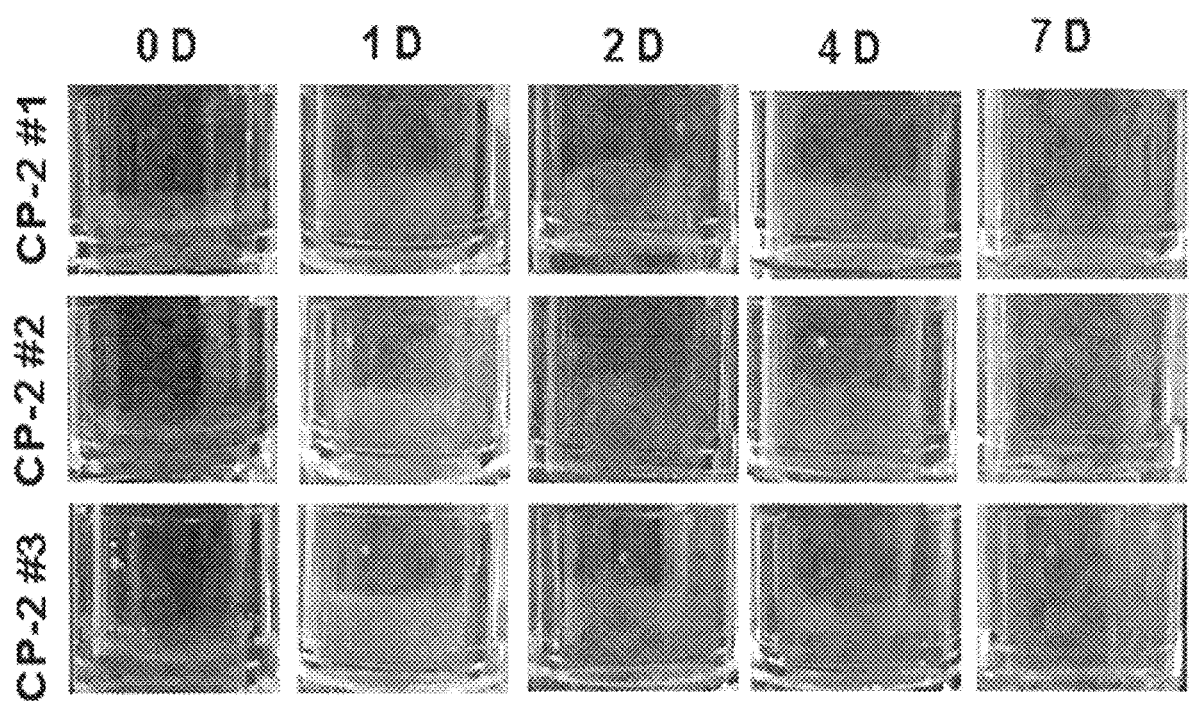

If the interaction between the I-5 hydrogel and macrophages significantly contributes to its bridging effect, injection of poly(organophosphazene) hydrogel without an imidazole ring structure would be predicted to result in expansion of cystic cavities. The present inventors have injected CP-2 hydrogel lacking the imidazole moiety and compared its effects to those of I-5. The viscosity at 37° C. of CP-2 was close to 600 Pa·s, which was very similar to that of I-5 (FIG. 13A). Furthermore, the in vitro stability test also showed that the dissolution of CP-2 occurred between day 4 and day 7 (FIG. 13B); that is, the physical properties of the two hydrogels are very similar. Unlike I-5, however, the injection of CP-2 lacking the imidazole moiety failed to eliminate large cystic cavities (FIGS. 12C and 12D).

Experimental Results 6

I-5 Injection Promotes Functional Recovery and Tissue Repair

To assess functional recovery after injection with I-5 or PBS, Basso-Beattie-Bresnahan (BBB) open field locomotor scores were determined during the 8 weeks after injury (7 weeks after PBS or I-5 injection).

Figure 14A:
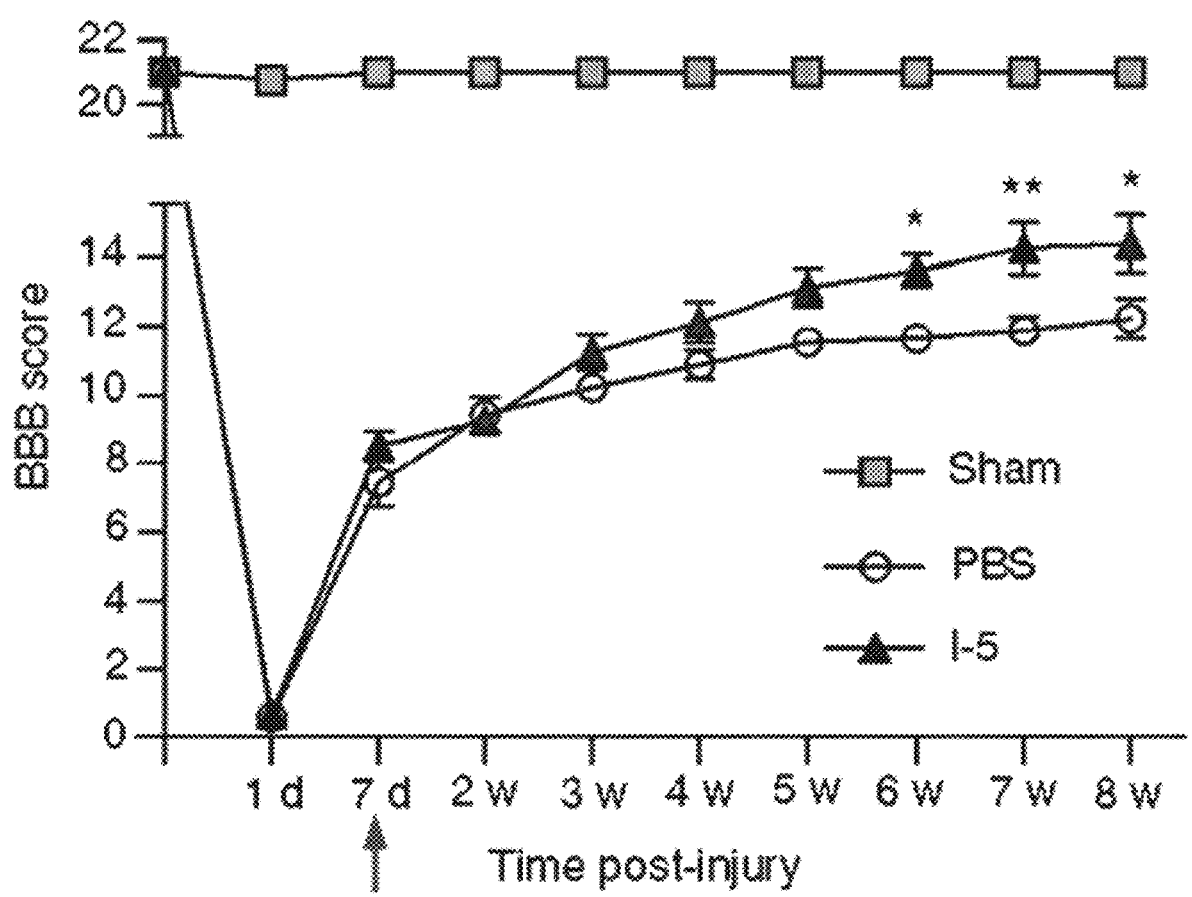

The animals in both groups showed spontaneous recovery over that timeframe (FIG. 14A). However, the animals injected with I-5 showed enhanced recovery from the 4 week time point and thereafter. Repeated measures of two-way ANOVA revealed a significant influence of I-5 treatment on behavioral recovery ($F_{(1, 120)}$=5.265, $p<0.05$), and the interaction between treatment and time points was also significant ($F_{(8, 120)}$=3.738, $p<0.001$).

Figure 14B:
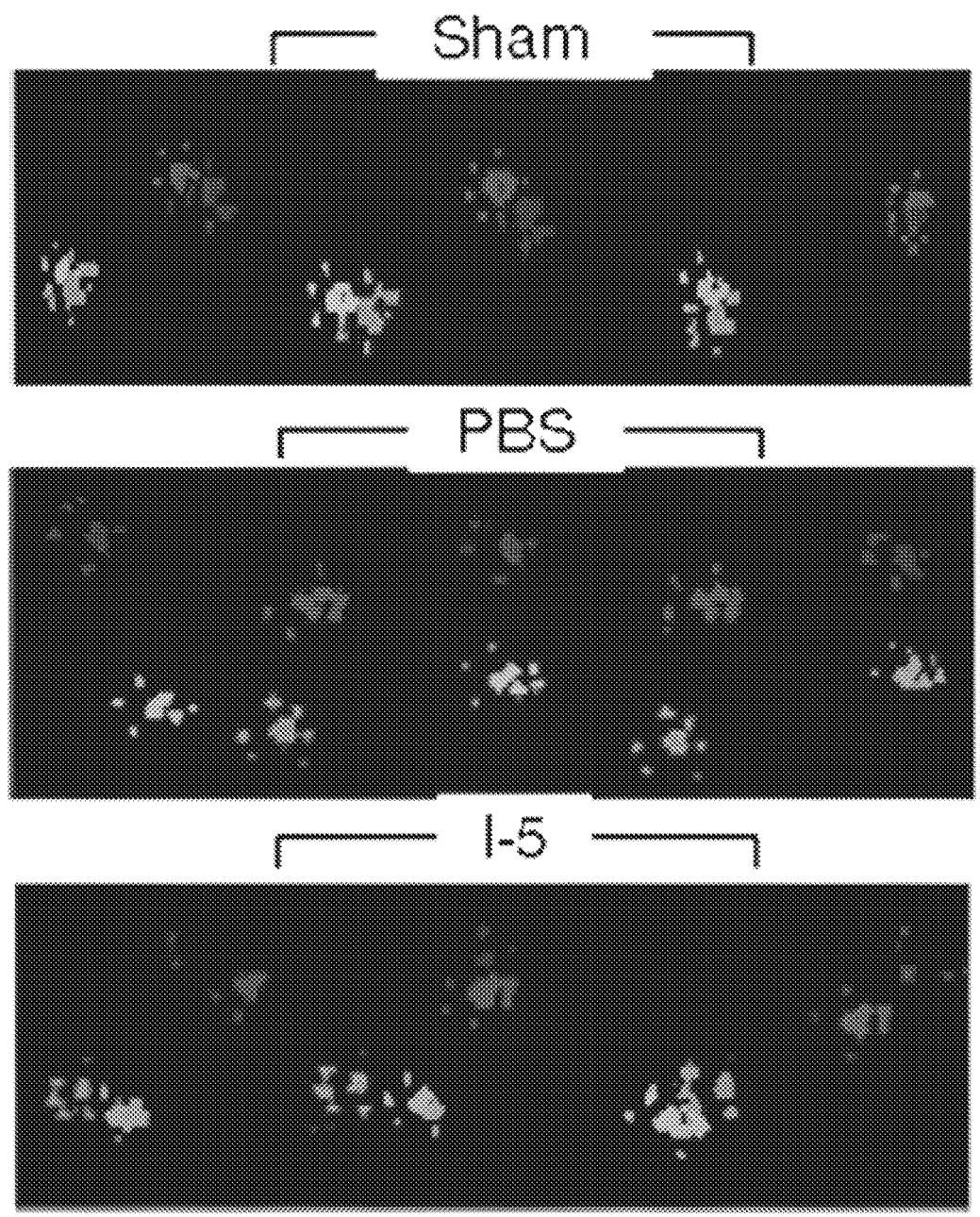
Figure 14C:
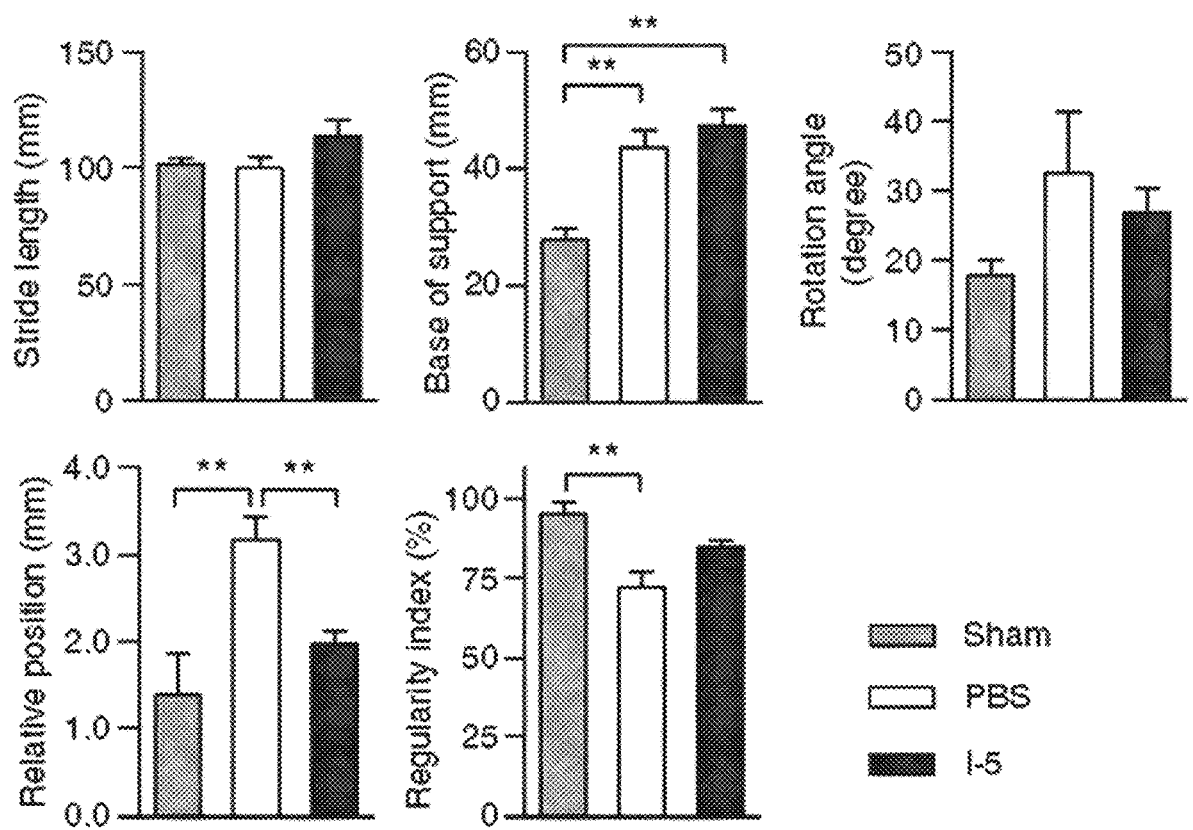

The present inventors have further tested locomotor recovery by Catwalk analysis (FIG. 14B). There was no significant difference in mean stride length between the treatment groups (including the sham-operated group) (FIG. 14C). Neither the base of support (the width between the left and right hindpaws) nor the angle of hindpaw rotation was improved after I-5 injection (FIG. 14C). The engagement of fore- and hindpaws during locomotion became uncoordinated after injury, resulting in non-overlapping fore- and hindpaw footprints (FIG. 14B) and an increase in relative position (the distance between the ipsilateral fore- and hindpaws in one step cycle) (FIG. 14C). The I-5 injection significantly reduced relative position, suggesting that the injection of I-5 resulted in enhanced coordination between the fore- and hindpaws. The regularity index, which was developed to determine coordinated gait, was significantly reduced after injury, and the I-5 injection tended to increase the regularity index (FIG. 14C).

Figure 15A:
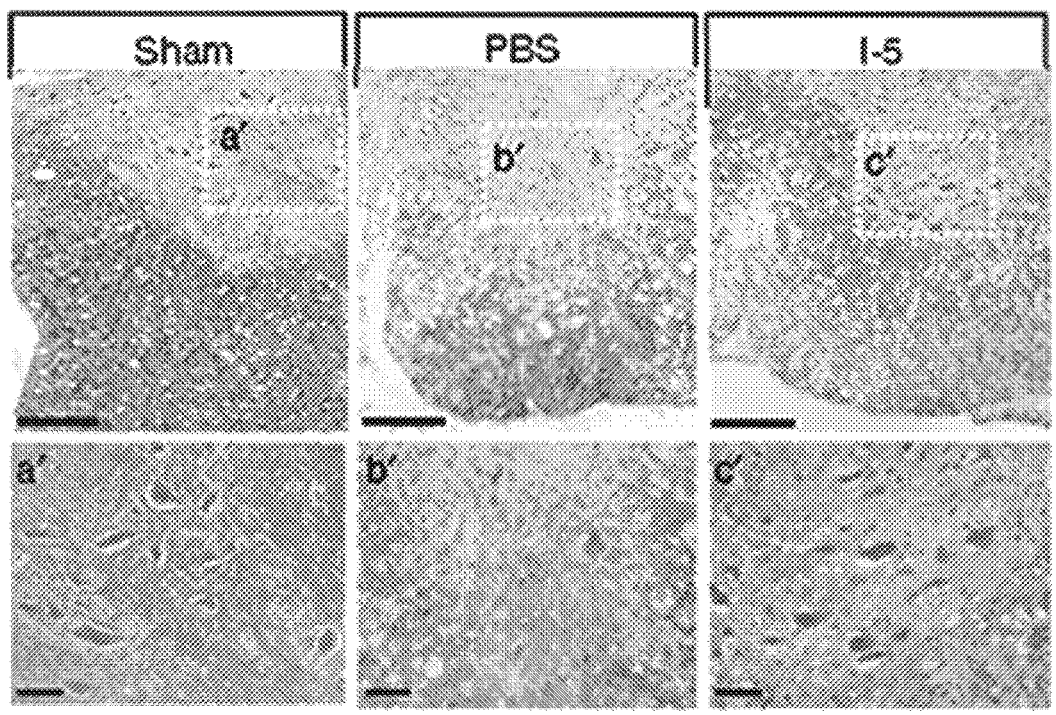
Figure 15B:
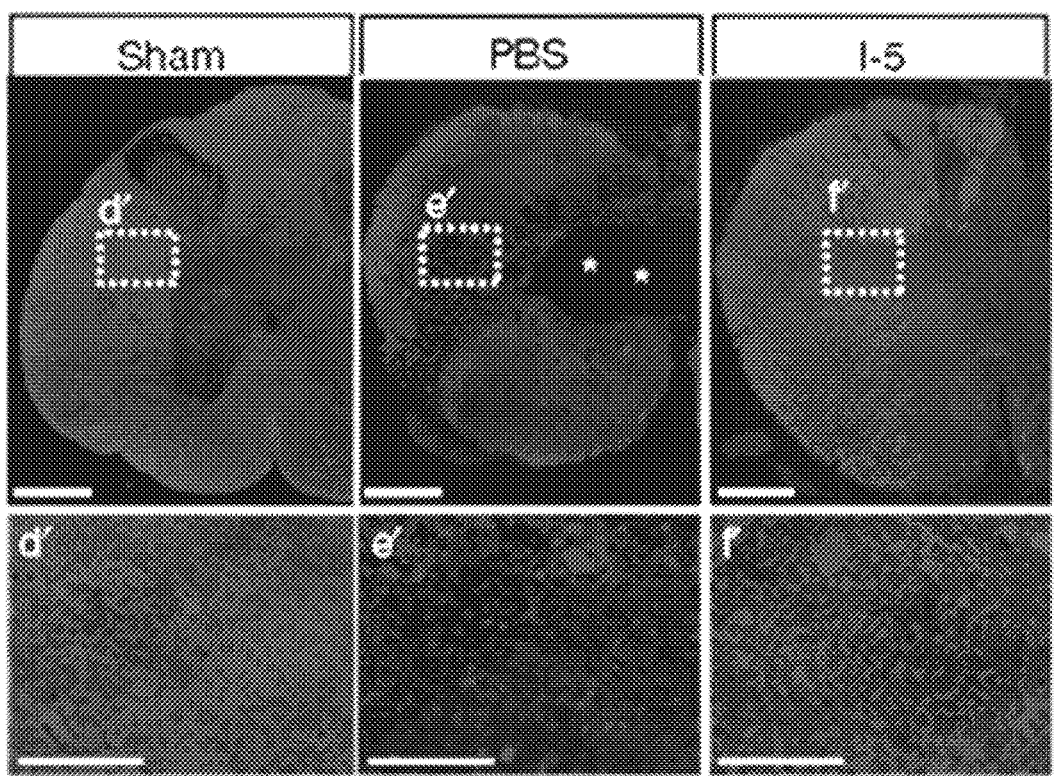
Figure 15C:
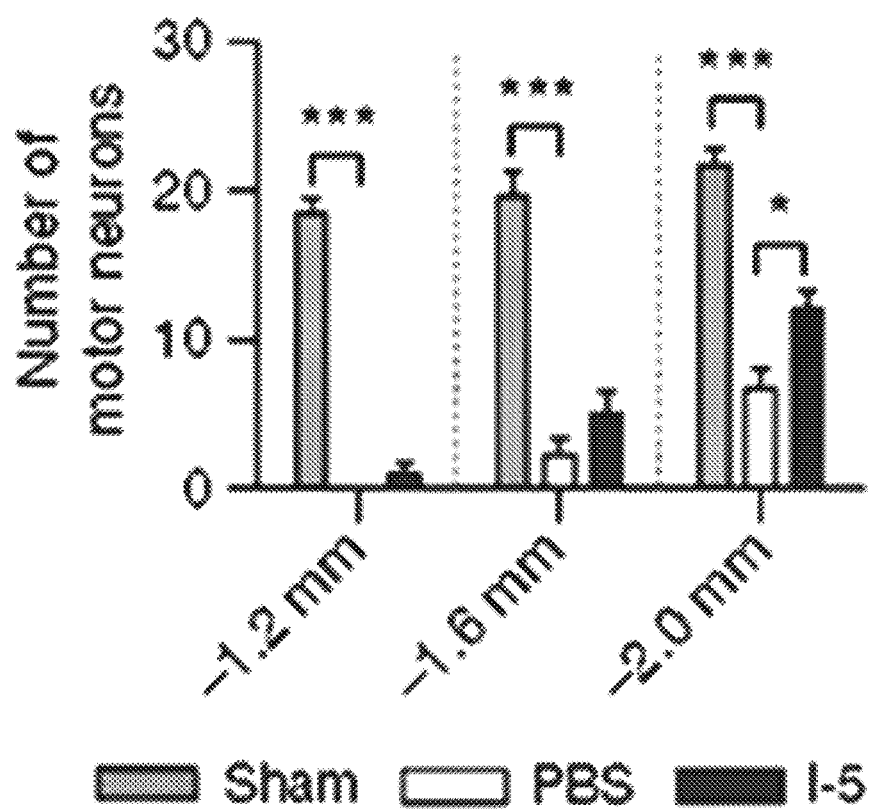
Figure 15D:
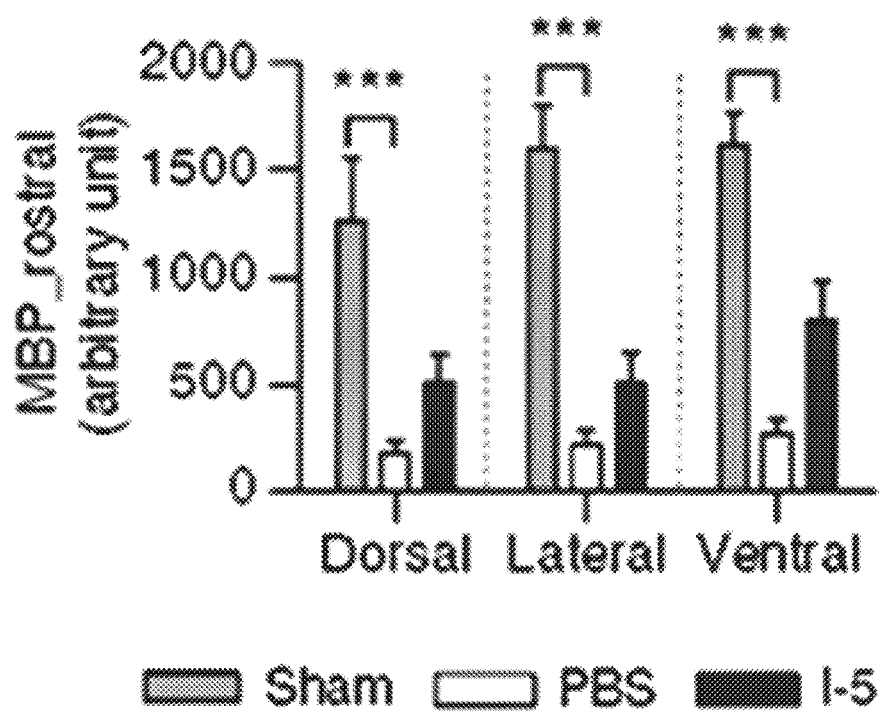
Figure 15E:
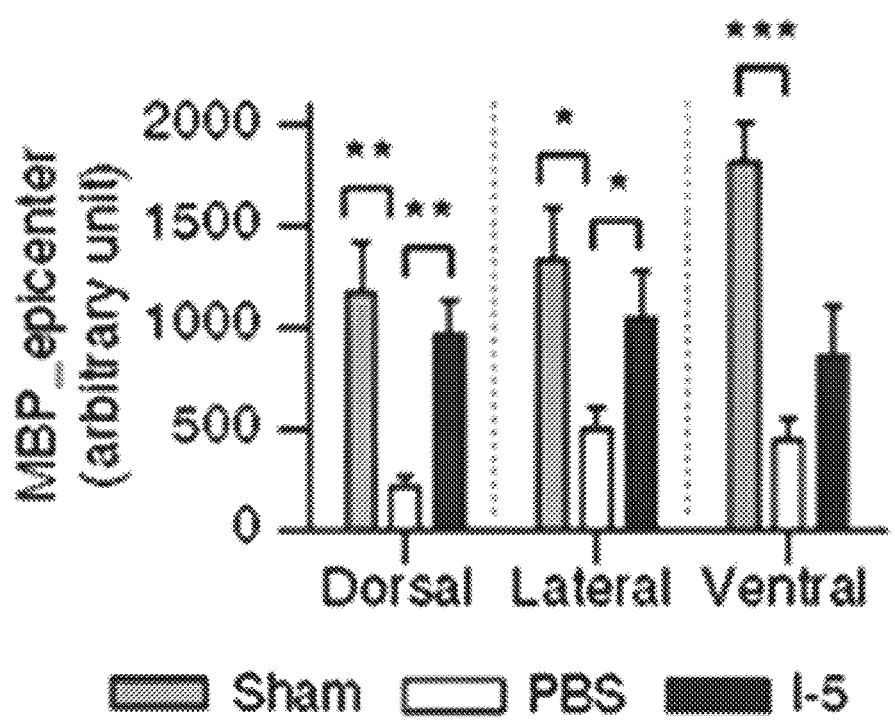
Figure 15F:
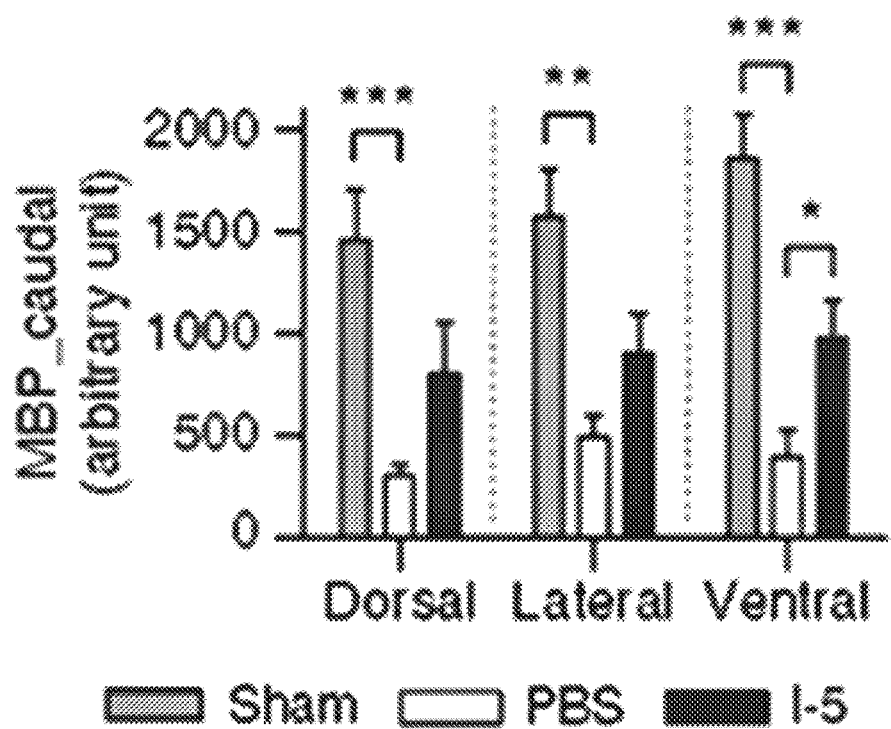

To examine the potential mechanisms by which I-5 injection enhances functional outcomes, the number of surviving motor neurons in the ventral horns caudal to the injury epicenter was analyzed 8 weeks after injury (FIG. 15A). Compared to the motor neurons in sham-operated animals, surviving neurons in the ventral horns were very rarely observed 1.2 mm caudal to the lesion in either group (FIG. 15A, PBS and I-5). At 1.6 mm caudal to the lesion, several motor neurons per section were observed with a tendency for the number to be higher in the I-5 injection group. The difference became statistically significant at 2.0 mm caudal to the lesion, where an average of more than 10 surviving neurons were found in the I-5 injection group (FIG. 15C). The present inventors have also noticed that myelin basic protein (MBP) immunoreactive signal intensity was significantly reduced in the white matter after injury, particularly in the white matter surrounding cystic cavities (FIG. 15B). In the animals injected with I-5, the MBP signal intensity was substantially increased (FIG. 15B). Quantification data showed that I-5 significantly increased the MBP immunoreactivity at the epicenter (FIG. 15E). The I-5 injection also tended to increase the MBP signal at both 2.0 mm rostral and caudal to the epicenter, especially in the ventral region (FIGS. 15D and 15F).

Figure 16A:
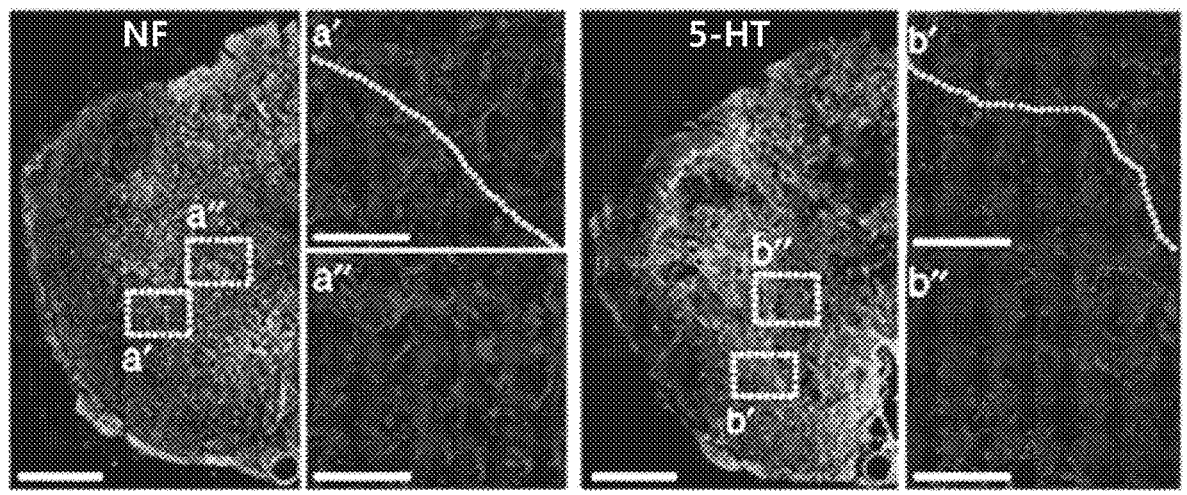
Figure 16B:
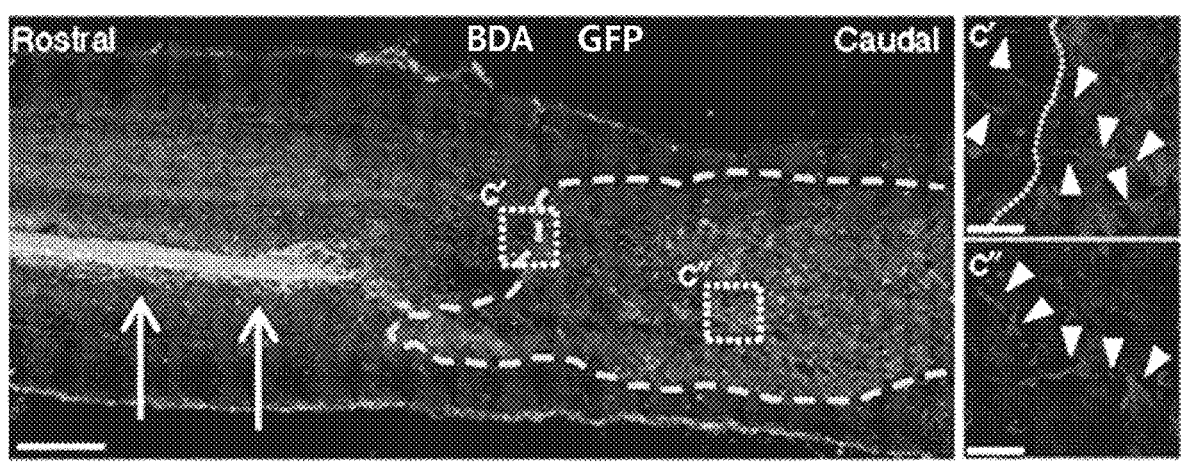

The present inventors have also examined whether regenerating axons could grow into the fibronectin-rich ECM. A substantial number of the neurofilament (NF)-positive axons were frequently observed within the newly-formed fibrotic matrix (FIG. 16A). Serotonergic (5-HT) axons, which may play a role in locomotor recovery, also grew into the fibronectin-rich matrix (FIG. 16A). The present inventors have also performed anterograde tracing. They injected AAV8-GFP into the sensorimotor cortex to visualize the corticospinal axon. GFP-positive corticospinal axons were nicely visualized up to several millimeters rostral to the epicenter, but then growing suddenly stopped (FIG. 16B). There were no discernible GFP-positive axonal fibers within the fibronectin-rich matrix (marked by the yellow dashed line). Next, biotinylated dextran amine (BDA) was injected into upper thoracic spinal cord to label various descending axons (either supraspinal or long propriospinal). Quite a large extent of BDA-traced axons grew beyond the rostral border of the fibronectin-rich matrix (FIG. 16B). The amount of axons visualized decreased in deeper areas farther from the border as the intensity of fibronectin immunoreactivity increased. Axonal fibers were occasionally observed in the central region of the fibronectin-rich matrix. However, there wereno BDA-traced axons regenerating beyond the caudal border of the fibronectin-rich matrix.

Figure 16C:
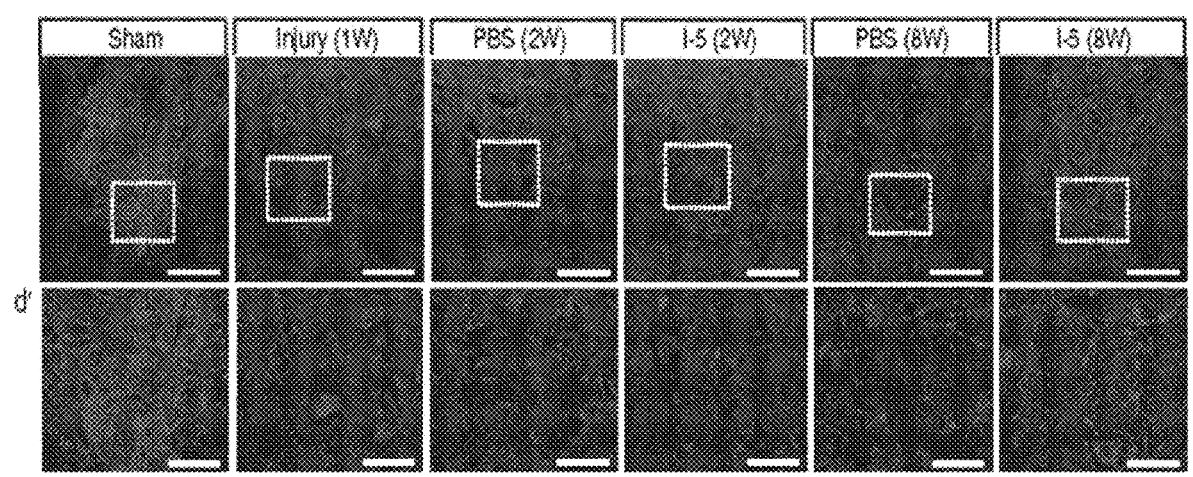
Figure 16D:
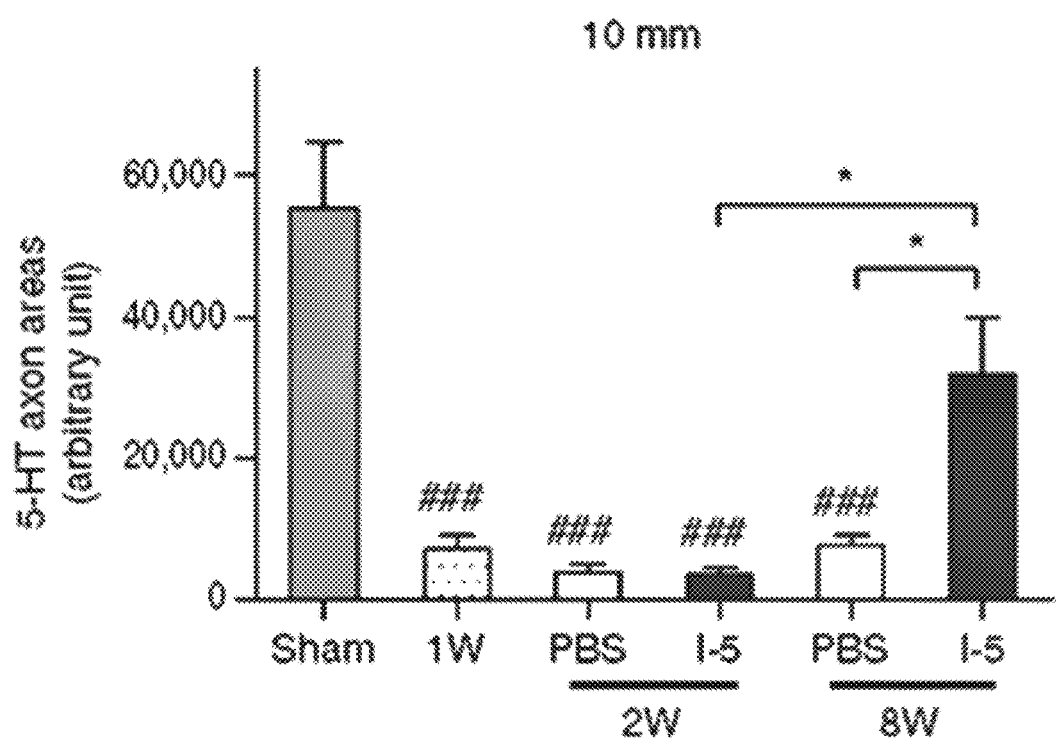
Figure 16E:
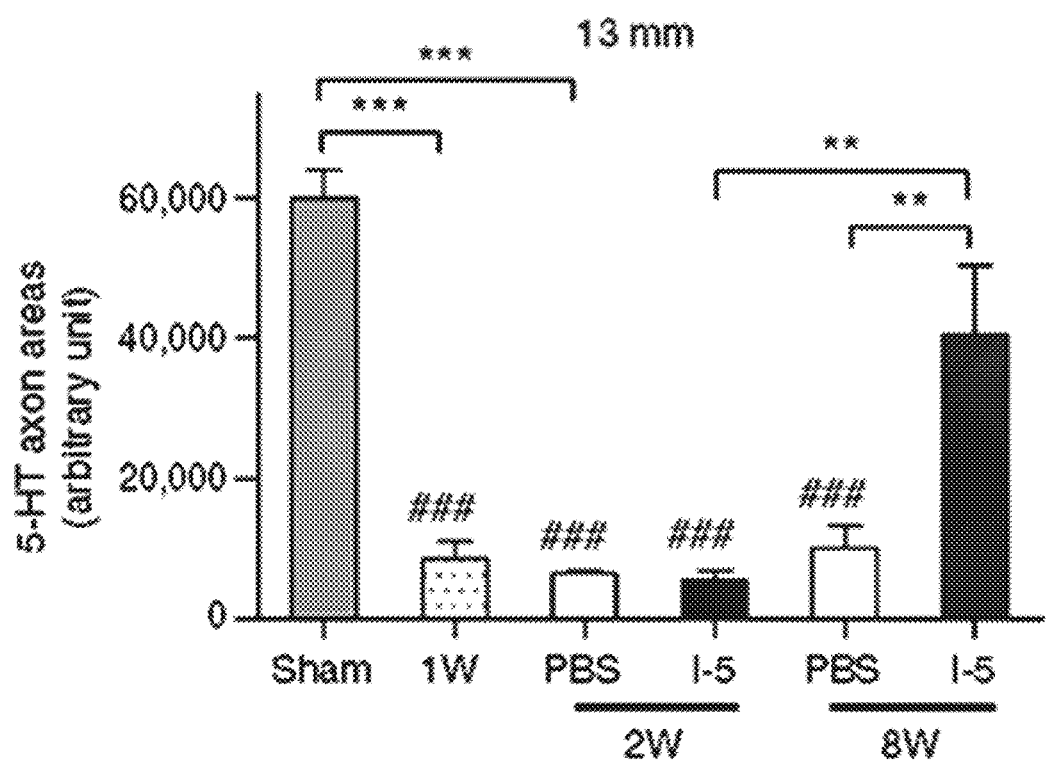

Finally, the present inventors have evaluated the extent of 5-HT axon innervation in the ventral motor regions of the lumbar spinal cord. At 1 week following injury, the density of 5-HT axons in the ventral horn of the lumbar spinal cord was sharply reduced compared to the sham-operated animals (FIGS. 16B and 16C). The 5-HT axon density did not significantly change for the next 7 days with injection of either PBS or I-5. However, the extent of 5-HT innervation increased substantially at the 8 week time point in animals injected with I-5, but not those injected with the PBS control (FIG. 16D). These results suggest that the fibronectin-rich matrix formed by I-5 injection may promote axonal reinnervation of the lumbar motor regions and thereby contribute to the recovery of locomotor function.

<Statistical Analysis>

Statistical analysis was performed using GraphPad Prism software (version 5.0). Unpaired Student's t-test (two-tailed) was used to compare the mean values of two groups. One-way ANOVA followed by Tukey's post hoc analysis was used for the mean comparison of three or more groups. Repeated-measures two-way ANOVA was used to compare differences in the BBB scores matched at different time points.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A method for treating spinal cord injury comprising administering a compound of Formula 1 below or a pharmaceutically acceptable salt thereof to a subject in need thereof:

[Formula 1]

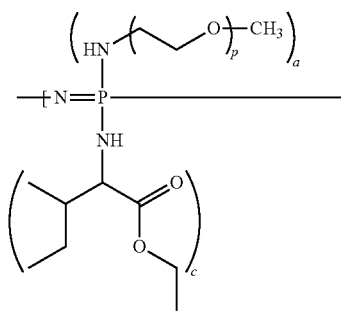

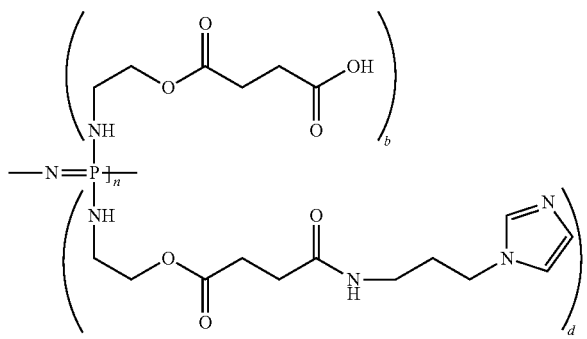

wherein, in Formula 1 above, p is in a range of 16 to 50, a, b, c, and d are values representing the amount of each substituent, which are each in a range of 0.01 to 1.9, the sum of (a+b+c+d) is 2, and n is a polymerization degree of polyphosphazene, which is in a range of 5 to 100,000.

2. The method of claim 1, wherein the compound of Formula 1 or pharmaceutically acceptable salt thereof removes cystic cavities in the spinal cord.

3. The method of claim 1, wherein the compound of Formula 1 or pharmaceutically acceptable salt thereof promotes regeneration of extracellular matrix (ECM).

4. The method of claim 1, wherein the spinal cord injury is at least one selected from the group consisting of flexion injury, vertical compression injury, hyperextension injury, flexion rotation injury, acute transverse myelitis, acute disseminated encephalomyelitis, myelopathy, non-Hodgkin's lymphoma, hydrocephalus, hereditary ataxia, neurosyphilis, Minamata disease, amyotrophic lateral sclerosis, and multiple sclerosis.

5. The method of claim 1, wherein the compound of Formula 1 or pharmaceutically acceptable salt thereof is able to treat spinal cord injury without the administration of additional cells or protein.

6. The method of claim 1, wherein the administration is an administration of a composition comprising the compound of Formula 1 or pharmaceutically acceptable salt thereof.

7. The method of claim 1, wherein the treatment is to ameliorate spinal cord injury.

8. A method for removing cystic cavities in the spinal cord comprising administering the compound of Formula 1 below or pharmaceutically acceptable salt thereof to a subject in need thereof:

[Formula 1]
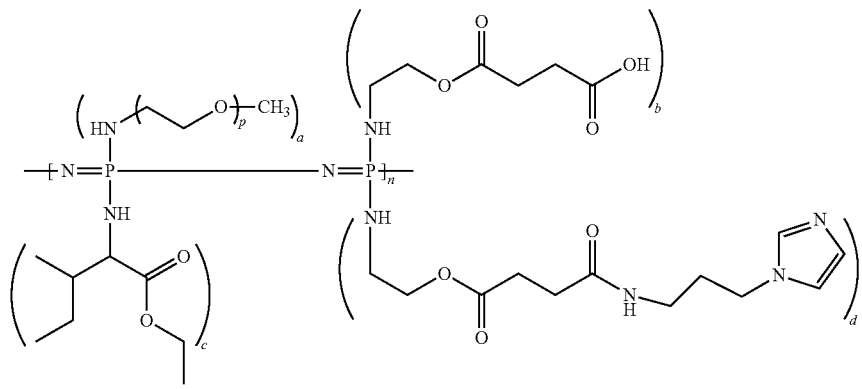
wherein, in Formula 1 above,
p is in a range of 16 to 50,
a, b, c, and d are values representing the amount of each substituent, which are each in a range of 0.01 to 1.9,
the sum of (a+b+c+d) is 2, and
n is a polymerization degree of polyphosphazene, which is in a range of 5 to 100,000.
* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: synthetic primer

<400> SEQUENCE: 1
ggcctatttc tgccatgaca aatac                                         25

<210> SEQ ID NO 2
<211> LENGTH: 20
<212> TYPE: DNA

```
<213> ORGANISM: artificial sequence
<220> FEATURE:
<223> OTHER INFORMATION: synthetic primer

<400> SEQUENCE: 2
ctgcaccgct gaagcaaaag                                              20

<210> SEQ ID NO 3
<211> LENGTH: 20
<212> TYPE: DNA
<213> ORGANISM: artificial sequence
<220> FEATURE:
<223> OTHER INFORMATION: synthetic construct

<400> SEQUENCE: 3
cgcggttcta ttttgttggt                                              20

<210> SEQ ID NO 4
<211> LENGTH: 20
<212> TYPE: DNA
<213> ORGANISM: artificial sequence
<220> FEATURE:
<223> OTHER INFORMATION: synthetic primer

<400> SEQUENCE: 4
agtcggcatc gtttatggtc                                              20
```